(12) United States Patent
Sridhar et al.

(10) Patent No.: US 11,912,660 B2
(45) Date of Patent: Feb. 27, 2024

(54) S6K1 PROTEIN KINASE INHIBITORS AS CANCER THERAPEUTICS

(71) Applicant: Xavier University of Louisiana, New Orleans, LA (US)

(72) Inventors: Jayalakshmi Sridhar, New Orleans, LA (US); Melyssa Bratton, New Orleans, LA (US); Rajesh Komati, Thibodaux, LA (US)

(73) Assignee: Xavier University of Louisiana, New Orleans, LA (US)

( * ) Notice: Subject to any disclaimer, the term of this patent is extended or adjusted under 35 U.S.C. 154(b) by 0 days.

(21) Appl. No.: 17/232,469

(22) Filed: Apr. 16, 2021

(65) Prior Publication Data

US 2021/0323919 A1 Oct. 21, 2021

Related U.S. Application Data

(60) Provisional application No. 63/011,765, filed on Apr. 17, 2020.

(51) Int. Cl.
*C07D 209/56* (2006.01)
*A61K 45/06* (2006.01)

(52) U.S. Cl.
CPC ............ *C07D 209/56* (2013.01); *A61K 45/06* (2013.01)

(58) Field of Classification Search
CPC .................................................. C07D 209/56
See application file for complete search history.

(56) References Cited

PUBLICATIONS

Gradler, et al. J. Mol. Biol. (2001) 306, 455-467.*
Zhou, et al. Med. Chem. Commun., 2016, 7, 292-296.*
Wu, et al. Journal of Applied Polymer Science, vol. 108, 2008, 2052-2059.*
"Cancer Facts & Figures", American Cancer Society, 2019, Atlanta.
Camila L. Amaral et al., "S6Ks isoforms contribute to viability, migration, docetaxel resistance and tumor formation of prostate cancer cells", BMC Cancer, 2016, pp. 1-9, vol. 16, No. 602.
Yong Zhang et al., "Prognostic value of phosphorylated mTOR/RPS6KB1 in non-small cell lung cancer", Asian Pacific Journal of Cancer Prevention, 2013, pp. 3725-3758, vol. 14, No. 6.
Di Wang et al., "Clinical significance of mTOR and p-mTOR protein expression in human colorectal carcinomas", Asian Pacific Journal of Cancer Prevention, 2011, pp. 2581-2584, vol. 12, No. 10.
Ji Chen et al., "A novel pathway regulating the mammalian target of rapamycin (mTOR) signaling", Biochemical Pharmacology, 2002, pp. 1071-1077, vol. 64, No. 7.
Farnaz Bahami-B et al., "p70 Ribosomal protein S6 kinase (Rps6kb1): an update", J. Clin. Pathol., 2014, pp. 1019-1025, vol. 67, No. 12.
Marina K. Holz, "The role of S6K1 in ER-positive breast cancer", Cell Cycle, 2012, pp. 3159-3165, vol. 11, No. 17.
Marina K. Holz et al., "mTOR and S6K1 mediate assembly of the translation preinitiation complex through dynamic protein interchange and ordered phosphorylation events", Cell, 2005, pp. 569-580, vol. 123, No. 4.
David Shahbazian et al., "The mTOR/PI3K and MAPK pathways converge on eIF4B to control its phosphorylation and activity", EMBO Journal, 2006, pp. 2781-2791, vol. 25, No. 12.
Chao Cai et al., "miR-195 Inhibits Tumor Progression by Targeting RPS6KB1 in Human Prostate Cancer", Clin. Cancer Res., 2015, pp. 4922-4934, vol. 21, No. 21.
Bojiang Chen et al., "Hyperphosphorylation of RPS6KB1, rather than overexpression, predicts worse prognosis in non-small cell lung cancer patients", PLoS One, 2017, pp. 1-16, vol. 12, No. 8.
Heba M. S. Ismail, Overexpression of s6 kinase 1 in brain tumours is associated with induction of hypoxia-responsive genes and predicts patients' survival, Journal of Oncology, 2012, pp. 1-10, vol. 2012.
Elin Karlsson et al., "Revealing Different Roles of the mTOR-Targets S6K1 and S6K2 in Breast Cancer by Expression Profiling and Structural Analysis", PLoS One, 2015, pp. 1-23, vol. 10, No. 12.
Ja Van Der Hage et al., "Overexpression of P70 S6 kinase protein is associated with increased risk of locoregional recurrence in node-negative premenopausal early breast cancer patients", British Journal of Cancer, 2004, pp. 1543-1550, vol. 90, No. 8.
Shuo Zhang et al., "The Prognostic Role of Ribosomal Protein S6 Kinase 1 Pathway in Patients With Solid Tumors: A Meta-Analysis", Frontiers Oncology, 2019, pp. 1-11, vol. 9, No. 390.
Ida Aronchik et al., "Novel potent and selective inhibitors of p90 ribosomal S6 kinase reveal the heterogeneity of RSK function in MAPK-driven cancers", Molecular Cancer Research, 2014, pp. 803-812, vol. 12, No. 5.
Rachel L. Yamnik et al., "mTOR/S6K1 and MAPK/RSK signaling pathways coordinately regulate estrogen receptor alpha serine 167 phosphorylation", FEBS Lett, 2010, pages, vol. 584, No. 1.
Diane C. Fingar et al., "mTOR controls cell cycle progression through its cell growth effectors S6K1 and 4E-BP1/eukaryotic translation initiation factor 4E", Molecular and Cellular Biology, 2004, pp. 200-216, vol. 24, No. 1.
Heidi A. Lane et al., "p70s6k function is essential for G1 progression", Nature, 1993, pp. 170-172, vol. 363, No. 6425.
Rachel L. Yamnik et al., "S6 kinase 1 regulates estrogen receptor alpha in control of breast cancer cell proliferation", The Journal of Biological Chemistry, 2009, pp. 6361-6369, vol. 284, No. 10.
William H. Chappell et al., "Ras/Raf/MEK/ERK and PI3K/PTEN/Akt/mTOR inhibitors: rationale and importance to inhibiting these pathways in human health", Oncotarget, 2011, pp. 135-164, vol. 2, No. 3.

(Continued)

*Primary Examiner* — Shawquia Jackson
(74) *Attorney, Agent, or Firm* — McBee, Moore & Vanik IP, LLC

(57) ABSTRACT

The present disclosure relates to compounds that act as protein kinase inhibitors, especially RPS6K1 and the synthesis of the same. Further, the present disclosure teaches the utilization of such compounds in a treatment for proliferative diseases, including cancer, particularly breast cancer, and especially ER+ and/or HER2+ breast cancer, prostate cancer, lung cancer, and metastatic cancer.

14 Claims, 3 Drawing Sheets

(2 of 3 Drawing Sheet(s) Filed in Color)

(56) References Cited

PUBLICATIONS

Linda S. Steelman et al., "Roles of the Raf/MEK/ERK and PI3K/PTEN/Akt/mTOR pathways in controlling growth and sensitivity to therapy-implications for cancer and aging", Aging, Albany, NY, 2011, pp. 192-222, vol. 3, No. 3.

Sylvain Couty et al., "The discovery of potent ribosomal S6 kinase inhibitors by high-throughput screening and structure-guided drug design", Oncotarget, 2013, pp. 1647-1661, vol. 4, No. 10.

D. Neise et al., The p90 ribosomal S6 kinase (RSK) inhibitor BI-D1870 prevents gamma irradiation-induced apoptosis and mediates senescence via RSK- and p53-independent accumulation of p21WAF1/CIP1, Cell Death Disease, 2013, pp. 1-11, vol. 4, e859.

Gopal P. Sapkota et al., "BI-D1870 is a specific inhibitor of the p90 RSK (ribosomal S6 kinase) isoforms in vitro and in vivo", Biochem J., 2007, pp. 29-38, vol. 401, No. 1.

Claudia Poleri et al., "Risk of recurrence in patients with surgically resected stage I non-small cell lung carcinoma: histopathologic and immunohistochemical analysis", Chest Journal, 2003; pp. 1858-1867, vol. 123, No. 6.

Giusy Di Conza et al. "The mTOR and PP2A Pathways Regulate PHD2 Phosphorylation to Fine-Tune HIF1α Levels and Colorectal Cancer Cell Survival under Hypoxia", Cell Reports, 2017; pp. 1699-1712, vol. 18, No. 7.

Tim R. Fenton et al., "Functions and regulation of the 70kDa ribosomal S6 kinases", The international Journal of Biochemistry & Cell Biology, 2011; pp. 47-59, vol. 43, No. 1.

Sejeong Shin et al., "Glycogen synthase kinase (GSK)-3 promotes p70 ribosomal protein S6 kinase (p70S6K) activity and cell proliferation", Proceedings of the National Academy of Sciences, 2011, pp. E1204-E1213, vol. 108, No. 47.

Ryan J. O. Dowling et al., "Dissecting the role of mTOR: lessons from mTOR inhibitors", Biochimica et Biophysica Acta, 2010, pp. 433-439, vol. 1804.

Walter Fischer et al., "92. Aromatic Nucleophilic Substitution, part I, Regiospecific Substitution of the Notrio Gropus in 3,5-Dinitrophthalic-Acid Derivatives1)", Helvetica Chimica Acta, 1985, pp. 846-853, vol. 68, No. 4.

Gautam Chattopadhyay et al., "Hydrazine-Hydroquinone Complex as an Efficient Solid Phase Hydrazine Donor: High Yield Synthesis of Luminol and Isoluminol", Journal of Chemical Research, 2011, pp. 326-328, vol. 35, No. 6.

\* cited by examiner

S6K1 PROTEIN KINASE INHIBITORS AS CANCER THERAPEUTICS

CROSS-REFERENCE TO RELATED APPLICATIONS

This application claims the benefit of U.S. Provisional Patent Application No. 63/011,765, filed 17 Apr. 2020. The disclosure of the priority application is incorporated in its entirety herein by reference.

STATEMENT REGARDING FEDERALLY SPONSORED RESEARCH OR DEVELOPMENT

This invention was made with government support under National Institutes of Health grants RL5GM118966, TL4M118968 and UL1GM118967 and the Bridge grant from Louisiana Cancer Research Consortium. The government has certain rights in the invention.

FIELD OF INVENTION

The present disclosure relates to compounds that inhibit S6K1 protein kinase. The disclosure also relates to pharmaceutical compositions comprising these protein kinase inhibitors, and methods for using the same for treatment of protein kinase-dependent diseases and conditions, including cancers.

BACKGROUND

1. Field

The present disclosure relates to compounds having, for example, activities as RPS6K1 protein kinase inhibitors, and methods for making the same. The disclosure also relates to pharmaceutical compositions comprising these protein kinase inhibitors, and methods for using the same for treatment of protein kinase-dependent diseases/conditions, including proliferative diseases such as cancer, and other diseases. Cancers for which these compounds may be useful include, but are not limited to, breast cancer, prostate cancer, non-small cell lung cancer, and metastatic cancer.

The compounds described here can provide effective therapy for breast cancers, especially estrogen receptor positive or "ER+" breast cancers or HER2-positive breast cancers.

2. Description of Related Art

It is estimated that in 2019, 20% (174,650 out of 870,970) of newly diagnosed male cancer patients were diagnosed with prostate cancer and 30% (268,600 out of 891,490) of newly diagnosed female cancer patients were diagnosed with breast cancer (1). In the same year (2019), it is estimated that 10% (31,620 out of 321,670) of deaths in male cancer patients were due to prostate cancer and 15% (41,760 out of 285,210) of deaths in female cancer patients were due to breast cancer. While the survival rates have improved over the last decade, and can be attributed to early detection and new treatment methods, the diagnosis of these cancers is still devastating for patients because the outcome cannot be predicted, and because survival varies by stage and age at diagnosis.

Serine/threonine kinases are a class of kinase enzymes that phosphorylates the —OH group of serine or threonine (which have similar side chains) with a phosphate group from adenosine triphosphate (ATP). Serine/threonine kinases are believed, by way of substrate phosphorylation, to play critical roles in signal transduction for a number of cell functions. Though the exact mechanisms of signal transduction are still unclear, serine/threonine kinases have been shown to be important contributing factors in cell proliferation, carcinogenesis and cell differentiation. Aberrant expression of protein kinases and their dysfunction are associated with several types of cancers. Accordingly, inhibitors of these serine/threonine kinases would be useful for the prevention and treatment chemotherapy of proliferative diseases dependent on these enzymes.

The ribosomal protein S6 Kinase proteins are members of the AGC family (named after the protein kinase A, G, and C families: PKA, PKC, PKG) of serine/threonine kinases and one of the main downstream effectors of the protein kinase B (AKT)/mammalian target of rapamycin (mTOR) pathway, which is a powerful stimulator of cell proliferation (2-3). This pathway is the most frequently activated pathway in cancer cells supporting tumor growth by activating transcription regulators such as hypoxia-inducible factor 1 (HIF-1) alpha (HIF1A) and ribosomal protein S6 Kinase B1 (S6K1) (4). Upon activation by mTOR, the S6K1 protein is primed to phosphorylate targets that promote protein synthesis and cell growth, such as ribosomal protein S6 (rpS6), eukaryotic translation initiation factor 4B (eIF4B), and eukaryotic elongation factor 2 kinase (eEF2K) (5-9). It has been shown by several studies that S6K1 is amplified in a variety of tumors, including breast cancer, prostate cancer, solid tumors, and metastatic cancers, and can correlate with unfavorable cancer prognosis (3, 7, 10-15). S6K1 has been shown to be regulated by several oncogenic pathways involving mTORC1, phosphoinositide 3-kinase (PI3K) pathways, extracellular signal-regulated kinase (ERK), and mitogen-activated protein kinase (MAPK) mediated pathways (7, 13-14, and 16-17). S6K1 mouse knockout studies have shown that S6K1 has an important role in cell proliferation through its targeting of 40S ribosomal protein S6, RNA processing and protein biogenesis. Overexpression of S6K1 imparts a significant advantage for proliferation in low serum conditions which is a hall mark of neoplastic transformation (18-20). RPS6K1 is one of the critical factors in protein synthesis. It has been found to play an important role in several human diseases including diabetes, obesity, cardiovascular diseases, hemangioma and proliferative diseases such as cancer and endometriosis (26-30). Due to the crucial role played by RPS6K1 in protein synthesis and its detrimental role in several human diseases ranging from diabetes and obesity to cancer, this protein is now emerging to be an important therapeutic target for drug development.

There are three major molecular subtypes of breast cancer based upon the presence or absence of two receptors. Accordingly, tumors expressing estrogen receptor (ER) are referred to as "ER+" breast cancers, and tumors expressing human epidermal growth factor 2 (HER2) are referred to as "HER2+" breast cancers. These types of cancers are treated with targeted therapies that block/inhibit growth of the cancer by interfering with the activity of a specific receptor that is responsible for the disease condition.

A significant number of breast cancers are ER+ breast cancers. In estrogen receptor positive breast cancer, tamoxifen is the most common treatment, but 20-30% of patients are resistant to tamoxifen. 20-30% of all breast cancers are HER2+ breast cancers. 70% of patients with HER2+ tumors demonstrate intrinsic or secondary resistance to trastuzumab, which is the most common treatment for this form of cancer.

S6K1 gene is amplified and overexpressed in about 10% of breast tumors and has been correlated with poor prognosis (14). Evidence has emerged of S6K1 playing an important role in ER-positive breast cancer and also HER2 positive breast cancer (7). S6K1 expression is estrogenically regulated and it has been shown that S6K1 directly phosphorylated and activated estrogen receptor alpha (ERα) (20). One of the most important factors is that upstream regulators that are frequently mutated in cancer, including PIK3Ca, phosphatase and tensin homolog (PTEN), AKT (protein kinase B), phosphoinositide-dependent kinase-1 (PDK1) and Tuberous sclerosis proteins 1 and 2 (TSC1/2; TSC1—hamartin; TSC2—tuberin), lead to hyperactivation of S6K1 (21-22). It has been determined that gain of S6K1 gene in ER-positive tumors is prognostic of metastatic capacity of human breast cancer (7). All of these evidences point to S6K1 being a prime target for therapeutic intervention.

A few compounds have emerged as ATP competitive inhibitors of S6K1, and some of them have shown promise in inhibiting the growth of breast cancer cells (16, 23-25). However, at present, there is no RPS6K1 inhibitor in therapeutic use in the clinic or known to be useful in this manner.

Given the prominent role that RPS6K1 plays in several types of cancer, there is a market and clinical need for more potent cancer drugs which target the protein kinase S6K1 by using RPS6K1 inhibitors.

BRIEF SUMMARY

The present disclosure relates generally to novel compounds and compositions useful for the inhibition of the ribosomal protein S6K1; compounds, intermediates, and methods of making such compounds and compositions; methods of using such compounds and compositions; pharmaceutical compositions comprising such compounds and compositions; and methods of using such pharmaceutical compositions, among other things.

In an embodiment, the present invention provides derivatives with the core structure isoindoline-1,3-dione (formula (Ia)), or a stereoisomer or pharmaceutically acceptable salt thereof.

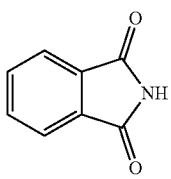

(formula (Ia))

In another embodiment, the present invention provides for derivatives of compounds of 4,6-diaminoisoindoline-1,3-dione (formula (Ib)), or a stereoisomer or pharmaceutically acceptable sale thereof.

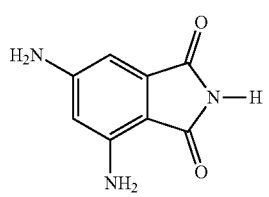

(formula (Ib))

In another embodiment, the present invention provides a compound of formula (IIa) or (IIb) or stereoisomers or pharmaceutically acceptable salts thereof:

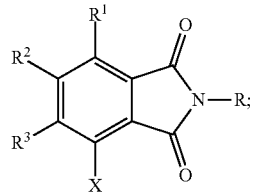

Formula (IIa)

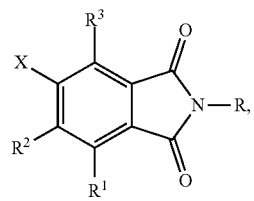

Formula (IIb)

wherein
R is H, alkyl, aryl, substituted aryl, hetereocyclyl, or substituted heterocyclyl;
X is —NHR$^4$, —NR$^5$COR$^5$, OH, or SH;
R$^1$, R$^2$ and R$^3$ are each independently selected from the group consisting of H, —NHR$^4$, OR$^4$, Br, Cl, I, —NH—CR$^4$=CR$^4$—, —NR$^5$—, —NR$^5$CH$_2$—, —CH$_2$NR$^5$—, —NR$^5$CO—, —NR$^5$COR$^5$, —CONR$^5$—, —N=N—, —NH—CO—NH—, —NH—CS—NH—, —CO—O—, CO—O—CH$_2$—, —SO$_2$NH—, —NH—SO$_2$—, —C≡C—, —O—CH$_2$—CO—, —OCH$_2$CH$_2$O—, —CH(OH)—, and —NO$_2$ bridging groups;
R$^4$ is selected from the group consisting of H, halogen, C$_{1-6}$ alkyl, C$_{1-6}$ alkenyl, C$_{1-6}$ alkoxy, C$_{1-6}$ haloalkyl, haloC$_{1-6}$ alkoxy, —COOH, —CONH$_2$, —COC$_{1-6}$ alkyl, O—C$_{1-6}$ alkyl, NH—C$_{1-6}$ alkyl, —S C$_{1-6}$ alkyl groups, —CN, —NH$_2$, and —NO$_2$; and
R$^5$ is selected from the group consisting of H, C$_{1-6}$ alkyl, aryl, C$_{3-8}$ cycloalkyl, monocyclic or bicyclic heterocyclyl, and monocyclic or bicyclic heteroaryl, wherein the aryl, heteroaryl or heterocyclyl groups may be optionally substituted by one or more R$^4$ groups.

In a further embodiment, X is , —NH$_2$, —NR$^5$COR$^5$, OH, or SH.

In a further embodiment, the compound is of formula (IIa), wherein:
R is H or alkyl;
X is NH$_2$;
R$^1$, R$^2$ and R$^3$ are each independently selected from the group consisting of H, —NHR$^4$, and —NR$^5$COR$^5$;
R$^4$ is selected from the group consisting of hydrogen, halogen, C$_{1-6}$ alkyl, O—C$_{1-6}$ alkyl, —CN, —NH$_2$, and —NO$_2$; and
R$^5$ independently represents hydrogen, heteroaryl, or aryl, wherein the heteroaryl or aryl group may be optionally substituted by one or more R$^4$ groups.

In a further embodiment, R is H.
In a further embodiment, R$^1$ and R$^3$ are H.
In a further embodiment, R$^2$ is —NR$^5$COR$^5$.
In a further embodiment, R$^4$ is selected from the group consisting of hydrogen, halogen, C$_{1-6}$ alkyl, O—C$_{1-6}$ alkyl, —CN, —NH$_2$, and —NO$_2$. In a further embodiment, R$^4$ is selected from the group consisting of hydrogen, halogen, —OCH$_3$, —CN, —NH$_2$, and —NO$_2$. In a further embodiment, R$^4$ is selected from the group consisting of hydrogen, halogen, and —NO$_2$.

In a further embodiment, R$^5$ independently represents hydrogen or thiophene or phenyl, wherein the thiophene or phenyl group may be optionally substituted by one or more R$^4$ groups. In a further embodiment, R$^5$ represents hydrogen or phenyl, wherein the phenyl group may be optionally substituted by one or more R$^4$ groups.

In a further embodiment, the compound is of formula (IIb), wherein:
R is H or alkyl;
X is NH$_2$ or —NR$^5$COR$^5$;
R$^1$, R$^2$ and R$^3$ are each independently selected from the group consisting of H, —NHR$^4$, and —NR$^5$COR$^5$;
R$^4$ is selected from the group consisting of hydrogen, halogen, C$_{1-6}$ alkyl, O—C$_{1-6}$ alkyl, —CN, —NH$_2$, and —NO$_2$; and
R$^5$ independently represents hydrogen, C$_{1-6}$ alkyl, heteroaryl, or aryl, wherein the heteroaryl or aryl group may be optionally substituted by one or more R$^4$ groups.

In a further embodiment, R is H or methyl.
In a further embodiment, R$^2$ and R$^3$ are H.
In a further embodiment, R$^1$ is NH$_2$ or —NR$^5$COR$^5$.
In a further embodiment, R$^4$ is selected from the group consisting of hydrogen, halogen, C$_{1-6}$ alkyl, O—C$_{1-6}$ alkyl, —CN, —NH$_2$, and —NO$_2$. In a further embodiment, R$^4$ is selected from the group consisting of hydrogen, halogen, —OCH$_3$, —CN, —NH$_2$, and —NO$_2$.

In a further embodiment, R$^5$ independently represents hydrogen, methyl, thiophene, or phenyl, wherein the thiophene or phenyl group may be optionally substituted by one or more R$^4$ groups. In a further embodiment, R$^5$ represents hydrogen or phenyl, wherein the phenyl group may be optionally substituted by one or more R$^4$ groups.

In a further embodiment, the compound of formula (IIa) and (IIb) is selected from the group consisting of:

RJ-1

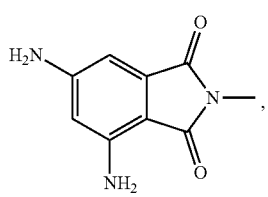

RJ-2

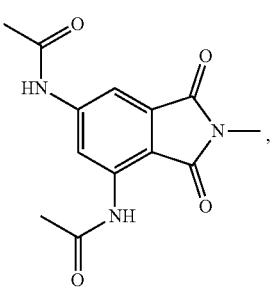

RJ-3

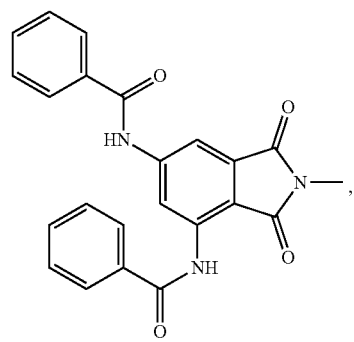

RJ-4

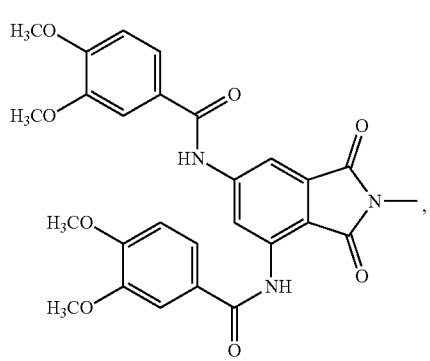

RJ-5

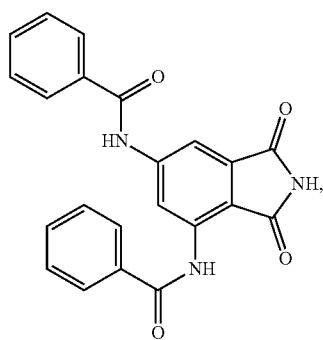

RJ-6

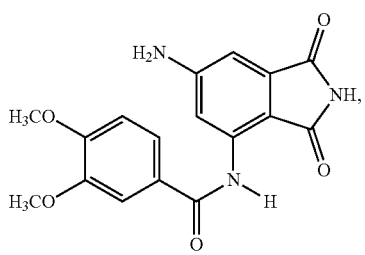

RJ-7a

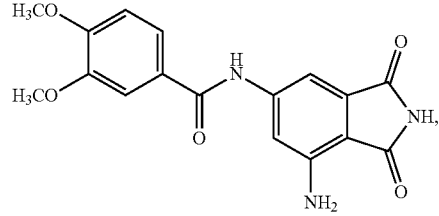

RJ-7

RJ-8
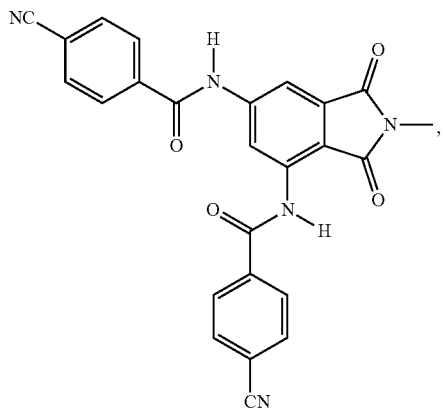
RJ-9
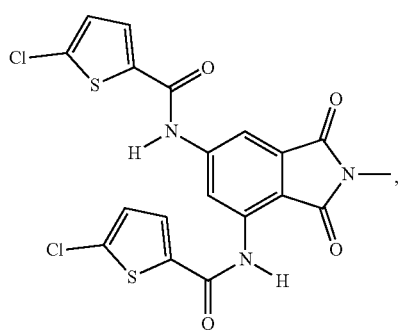
RJ-10
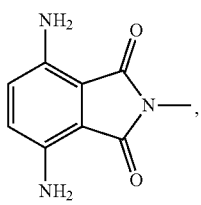
RJ-11
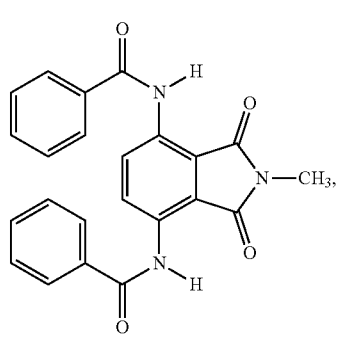
RJ-12
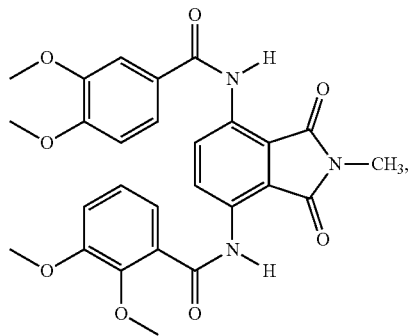
RJ-13
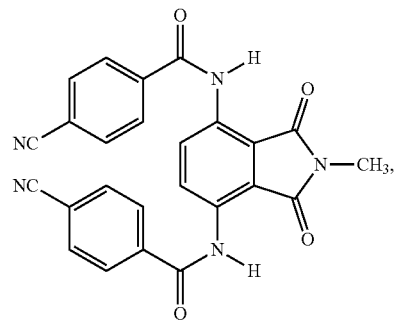
RJ-14
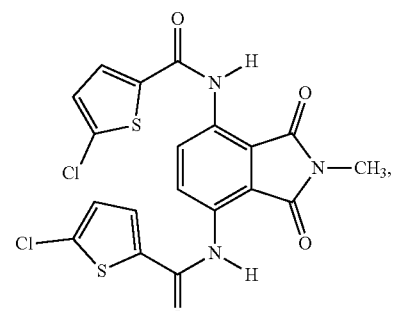
RJ-15
RJ-16
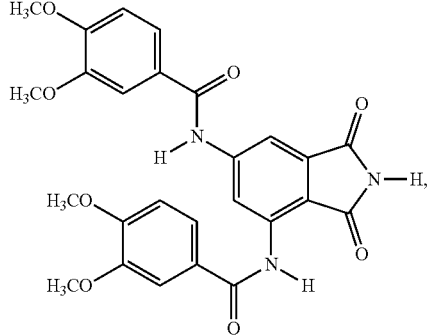

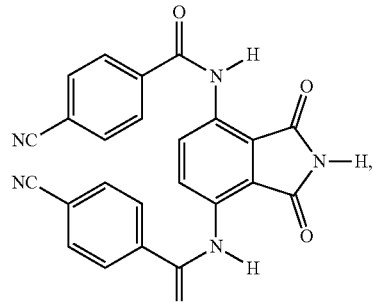
RJ-17
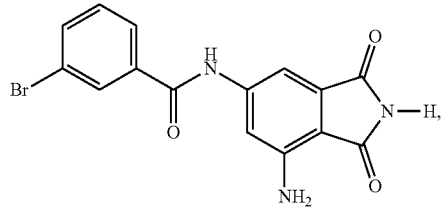
RJ-23
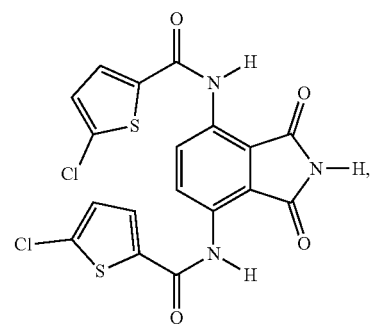
RJ-18
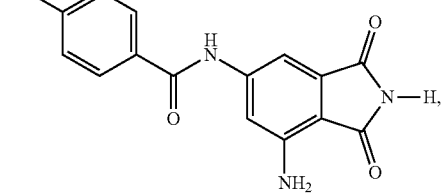
RJ-24
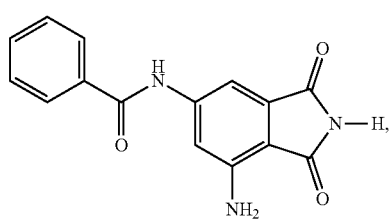
RJ-19
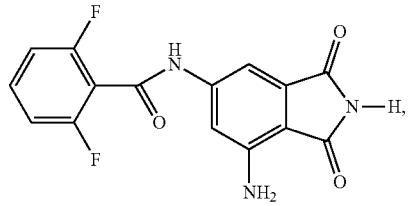
RJ-25
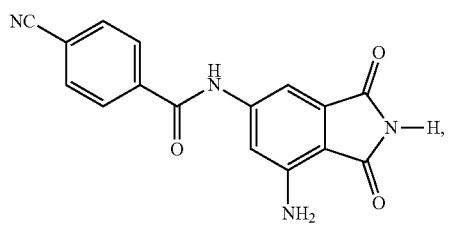
RJ-20
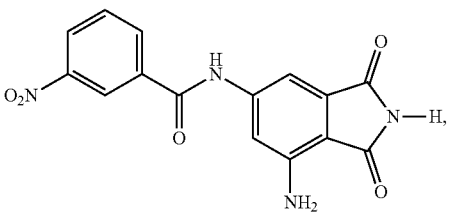
RJ-26
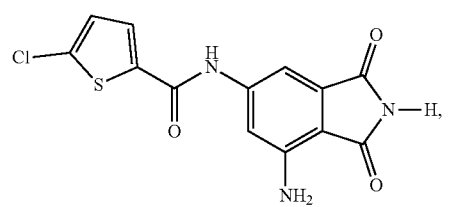
RJ-21
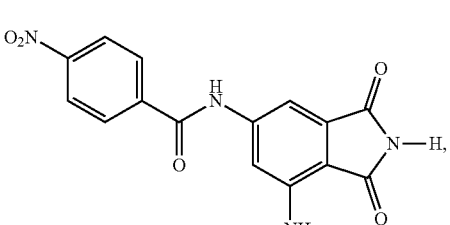
RJ-27
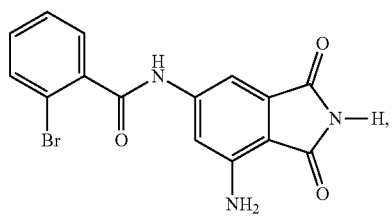
RJ-22
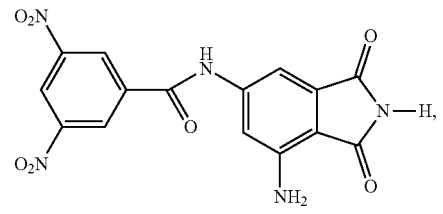
RJ-28
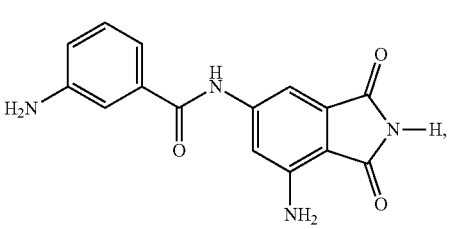
RJ-29

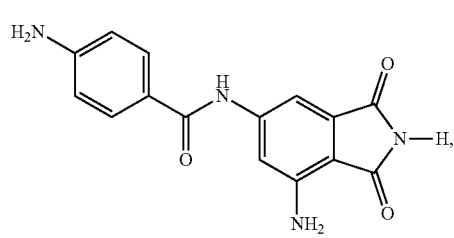
RJ-30
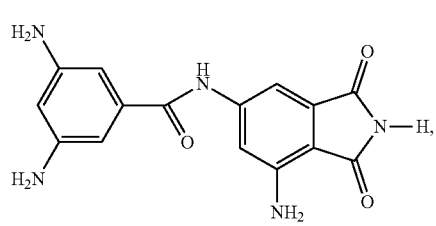
RJ-31
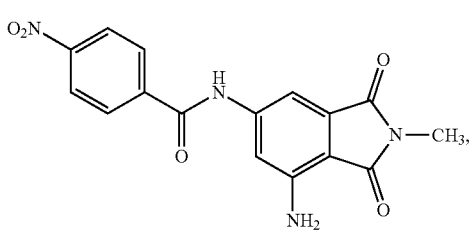
RJ-32
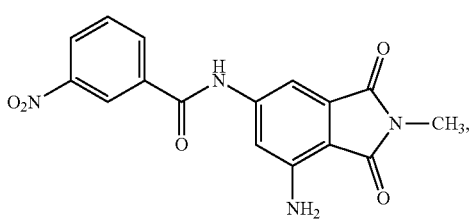
RJ-33
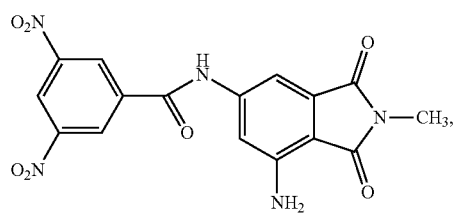
RJ-34
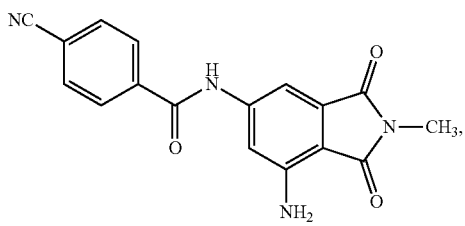
RJ-35
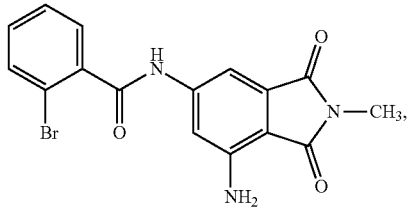
RJ-36
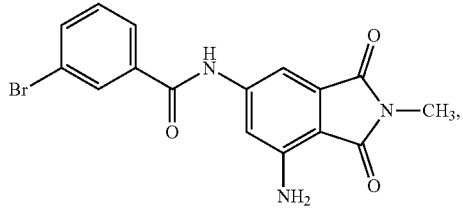
RJ-37
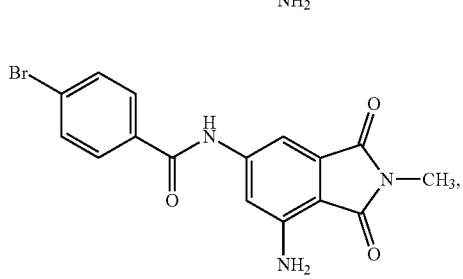
RJ-38
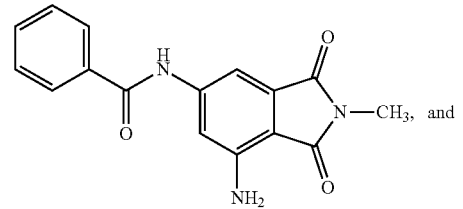
RJ-39
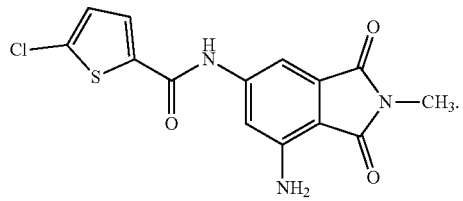
RJ-40
In a further preferred embodiment, the compound is a compound of formula (IIa), and is selected from the group consisting of:
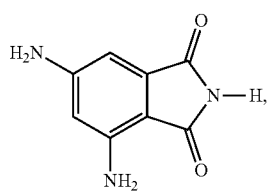
RJ-1

-continued
RJ-7
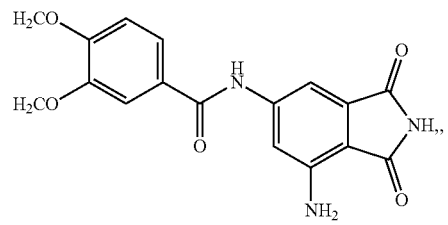
RJ-19
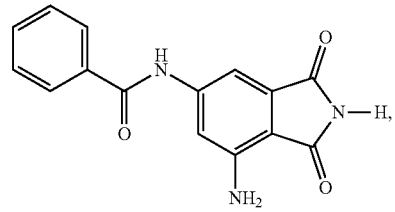
RJ-20
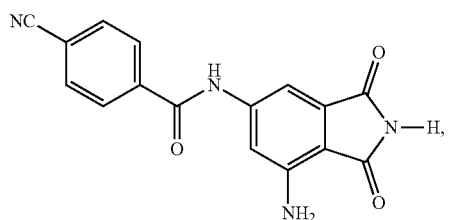
RJ-21
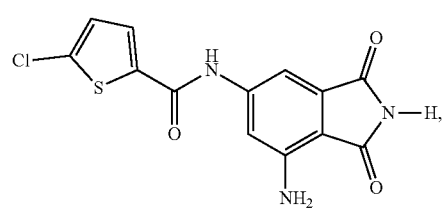
RJ-22
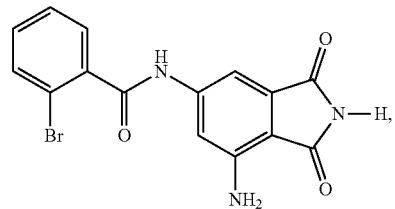
RJ-23
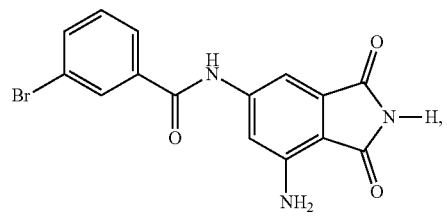
RJ-24
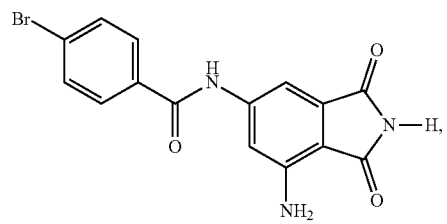
RJ-25
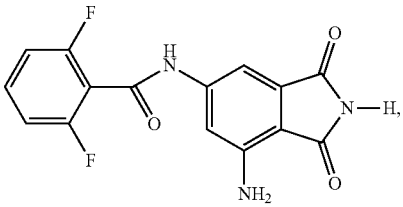
RJ-26
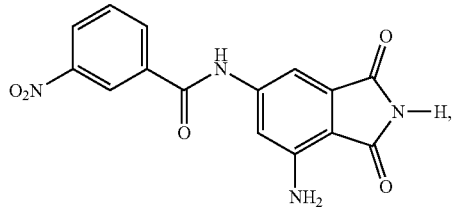
RJ-27
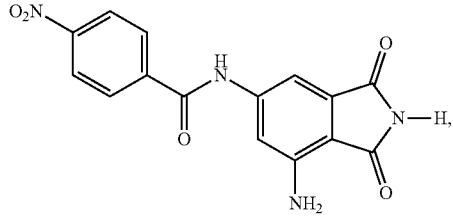
RJ-28
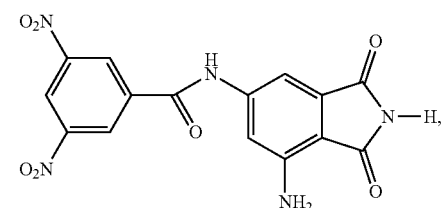
RJ-29
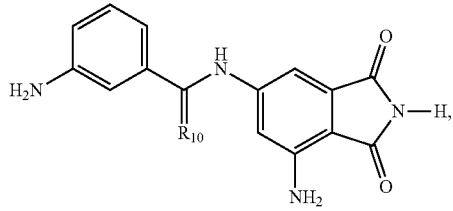
RJ-30
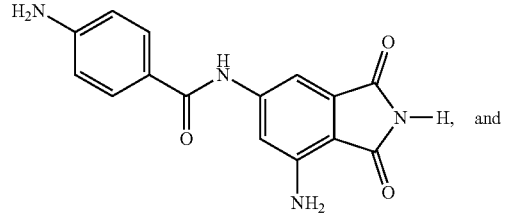
and
RJ-31
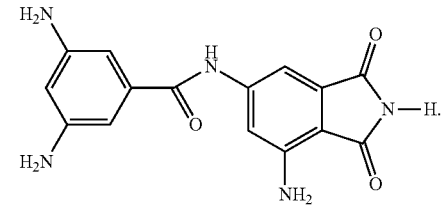
In a further embodiment, the compound of formula (IIa) is

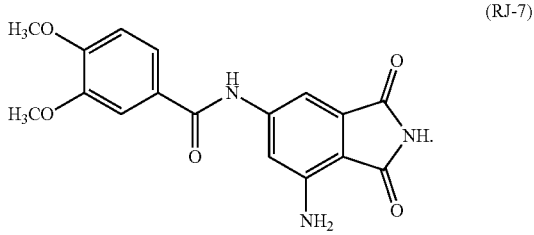 [SMILES: COc1ccc(C(=O)Nc2cc(N)c3c(c2)C(=O)NC3=O)cc1OC]
(RJ-7)

An exemplary scheme for synthesizing the compound of Formula (RJ-7) is discussed below in the Examples.

In a further embodiment, the compound of formula (IIa) is:

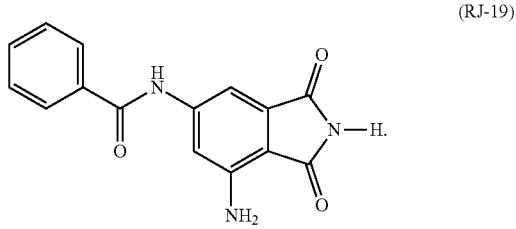
(RJ-19)

An exemplary scheme for synthesizing the compound of Formula (RJ-19) is discussed below in the Examples.

In a further embodiment, the compound of formula (IIa) is

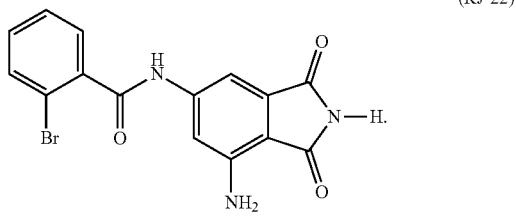
(RJ-22)

An exemplary scheme for synthesizing the compound of Formula (RJ-22) is discussed below in the Examples.

In a further embodiment, the compound of formula (IIa) is

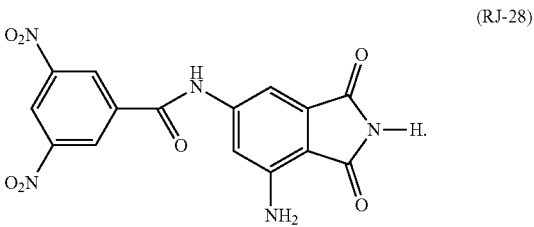
(RJ-28)

An exemplary scheme for synthesizing the compound of Formula (RJ-28) is discussed below in the Examples.

In an embodiment, the disclosure provides for a pharmaceutical composition comprising at least one compound of formula (IIa) or (IIb) or a pharmaceutically acceptable salt or solvate thereof. In an embodiment, the pharmaceutical compound is for use in (or useful for) treatment of a proliferative disease, such as endometriosis, a cancer, for example, breast cancer, prostate cancer, lung cancer, metastatic cancer, endometrial cancer, neuroendocrine tumor, pancreatic ductal adenocarcinoma and diseases including diabetes, obesity and hemangioma, etc. A further embodiment provides a method of treating cancer comprising administering to a subject (e.g., a mammal, preferably a human mammal) a compound according to any one of the preceding paragraphs. In an embodiment, the cancer can be breast cancer, prostate cancer, lung cancer (non-small cell lung cancer), metastatic cancer, or solid tumors. An embodiment may provide use of a compound as discussed herein for treating ER-positive cancer or HER2 positive cancer. An embodiment may provide use of a compound as in the paragraphs above for treating breast cancer in a subject in need thereof. In some embodiments the breast cancer is an ER-positive breast cancer or HER2 positive breast cancer. An embodiment may provide use of a compound as in the paragraphs above for treating prostate cancer in a subject in need thereof. In some embodiments a compound as presented above is used in the preparation of a medicament for treatment of breast cancer.

The pharmaceutical compositions of the present disclosure can be in any form known to those of skill in the art. For instance, in some embodiments the pharmaceutical compositions are in a form of a product for oral delivery, said product form being selected from a group consisting of a concentrate, dried powder, liquid, capsule, pellet, and pill. In other embodiments, the pharmaceutical compositions of the disclosure are in the form of a product for parenteral administration including intravascular (intraarterial, intravenous), intraparenchymal, intradermal, subdermal, intramuscular, intratumor, intraperitoneal, intralymphatic, intrathecal, subdural, epidural, and subcutaneous administration. The pharmaceutical compositions disclosed herein may also further comprise carriers, binders, diluents, and excipients.

Also, in other aspects, the present disclosure relates to a protein kinase RPS6K1 inhibitor composition comprising one or more compounds selected from the group consisting of a compound of Formula (IIa), Formula (IIb), their derivatives, and pharmaceutically acceptable salts (salt forms such as Chloride, Acetate, Aspartate, Benzenesulfonate, Benzoate, Besylate, Bicarbonate, Bitartrate, Bromide, Camsylate, Carbonate, Citrate, Decanoate, Edetate, Esylate, Fumarate, Gluceptate, Gluconate, Glutamate, Glycolate, Hexanoate, Hydroxynaphthoate, Iodide, Isethionate, Lactate, Lactobionate, Malate, Maleate, Mandelate, Mesylate, Methylsulfate, Mucate, Napsylate, Nitrate, Octanoate, Oleate, Pamoate, Pantothenate, Phosphate, Polygalacturonate, Propionate, Salicylate, Stearate, Succinate, Sulfate, Tartrate, Teoclate, Tosylate, etc.) and solvates (hydrates and other solvates) thereof. In an embodiment, said one or more compounds has a purity of ≥75%, ≥80%, ≥85%, ≥90%, ≥95%, ≥96%, ≥97%, or ≥98%, and ≥99%.

In an embodiment, a pharmaceutical composition is provided comprising the claimed protein kinase RPS6K1 inhibitor composition, either alone or in combination with at least one additional therapeutic agent, with a pharmaceutically acceptable carrier. In an embodiment, uses (methods of use) are provided for the claimed protein kinase RPS6K1 inhibitor compositions, either alone or in combination with at least one additional therapeutic agent, with or without a pharmaceutically acceptable carrier, in the treatment of proliferative diseases including prostate cancer, breast cancer, lung cancer (non-small cell), metastatic cancer, or solid tumors at any stage of the disease diagnosis. The combination with an additional therapeutic agent may take the form of combining the claimed at least one protein kinase inhibitor compound with any known therapeutic agent or agents.

The methods for treating a clinical indication by the protein kinase inhibitor compounds disclosed herein, may be effectuated by administering a therapeutically effective amount of the protein kinase inhibitor compounds to a patient in need thereof. This therapeutically effective amount may comprise administration of the prodrug to the patient at 1 mg/kg/day, 2 mg/kg/day, 3 mg/kg/day, 4 mg/kg/day, 5 mg/kg/day, 10 mg/kg/day and 20 mg/kg/day. Alternatively, amounts ranging from about 0.001mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to 10 mg/kg/day, or about 10 mg/kg/day to about 100 mg/kg/day are also contemplated. Administration to a patient in need thereof may occur once, twice, three times, or four times per day.

A further object of the disclosure is a kit, comprising a composition containing at least one protein kinase inhibitor compounds disclosed herein for treatment and prevention of cancer and cancer related morbidities. The composition of the kit may comprise at least one carrier, at least one binder, at least one diluent, at least one excipient, at least one other therapeutic agent, or mixtures thereof.

One aspect of the present disclosure is the compounds disclosed herein as well as the intermediates as used for their synthesis.

While certain features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is expressly stated as being "critical" or "essential."

These and other features, aspects, and advantages of embodiments of the present disclosure will become better understood with regard to the following descriptions, claims, and accompanying drawings explained below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a further understanding of the nature, objects, and advantages of the present disclosure, reference should be had to the following detailed description, read in conjunction with the following drawings, wherein like reference numerals denote like elements.

DETAILED DESCRIPTION

Figure 1:
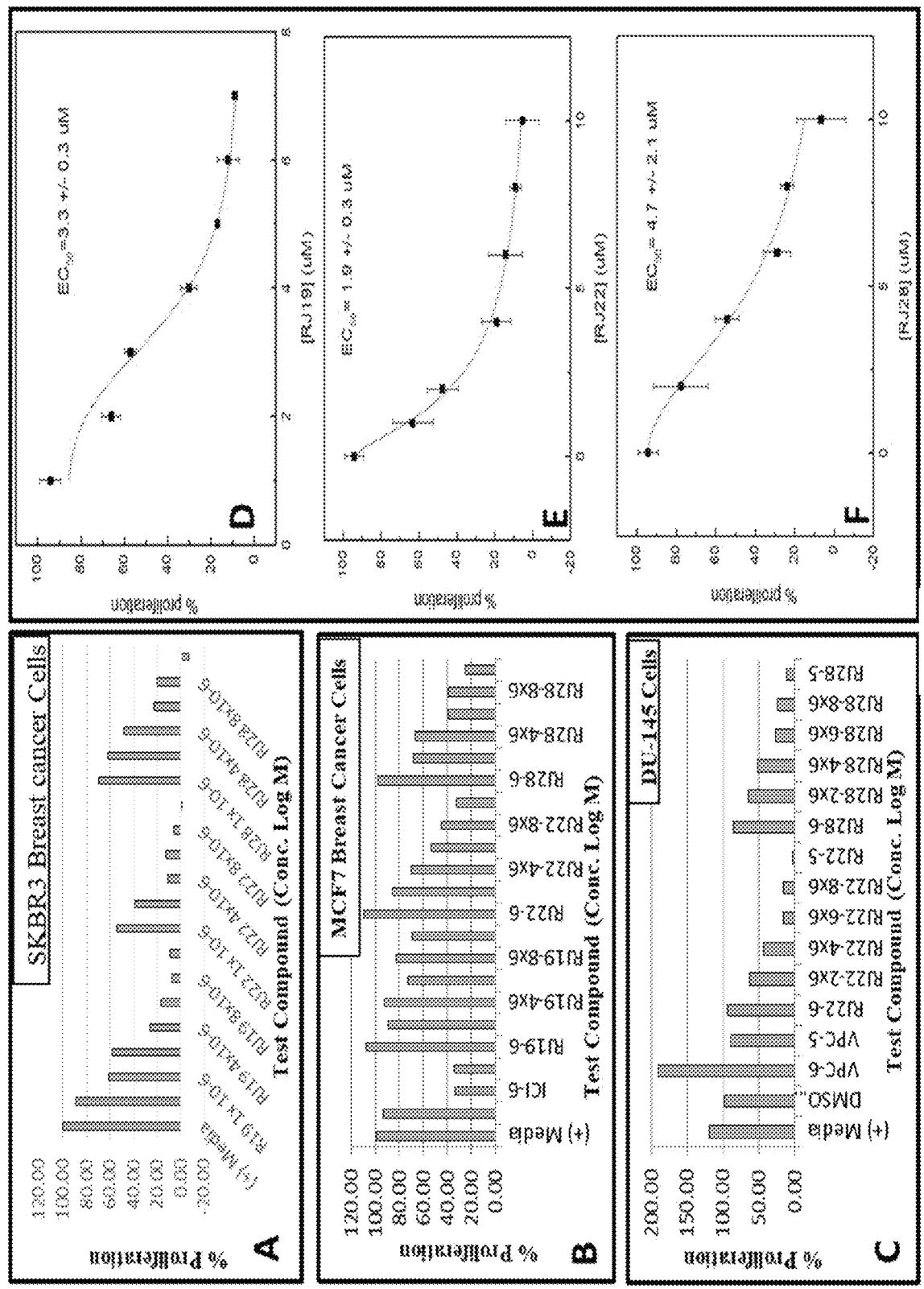
FIG. 1 shows growth inhibition of (A) HER2 positive (SKBR3), (B)ER-positive (MCF7) breast cancer cell lines and (C) prostate cancer cell line (DU-145) by the three compounds RJ19, RJ22 and RJ28. (D), (E) and (F) show the dose response curves of growth inhibition of SKBR3 breast cancer cell line.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

As used herein, the term "minimize" or "reduce", or derivatives thereof, include a complete or partial inhibition of a specified biological effect (which is apparent from the context in which the terms "minimize" or "reduce" are used).

The compounds according to the disclosure are isolated and purified in a manner known per se, e.g., by distilling off any solvent in vacuo and recrystallizing the residue obtained from a suitable solvent or subjecting it to a customary purification method, such as chromatography on a suitable support material. Furthermore, reverse phase preparative HPLC of compounds of the present disclosure, which possess a sufficiently basic or acidic functionality, may result in the formation of a salt, such as, in the case of a compound of the present disclosure which is sufficiently basic, a trifluoroacetate or formate salt for example, or, in the case of a compound of the present disclosure which is sufficiently acidic, an ammonium salt for example. Salts of this type can either be transformed into their free base or free acid form, respectively, by various methods known to the person skilled in the art, or can be used as salts in subsequent biological assays. Additionally, the drying process during the isolation of compounds of the present disclosure may not fully remove traces of cosolvents, especially such as formic acid or trifluoroacetic acid, to give solvates or inclusion complexes. The person skilled in the art will recognize which solvates or inclusion complexes are acceptable to be used in subsequent biological assays. It is to be understood that the specific form (e.g., salt, free base, solvate, inclusion complex) of a compound of the present disclosure as isolated as described herein is not necessarily the only form in which said compound can be applied to a biological assay in order to quantify the specific biological activity.

One aspect of the disclosure is salts of the compounds according to the disclosure including all inorganic and organic salts, especially all pharmaceutically acceptable inorganic and organic salts, particularly all pharmaceutically acceptable inorganic and organic salts customarily used in pharmacy.

Examples of salts include, but are not limited to, lithium, sodium, potassium, calcium, aluminum, magnesium, titanium, meglumine, ammonium, salts optionally derived from $NH_3$ or organic amines having from 1 to 16 C-atoms such as, e.g., ethylamine, diethylamine, triethylamine,ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperindine and guanidinium salts.

The salts include water-insoluble and, particularly, water-soluble salts.

As used herein, "pharmaceutically acceptable salts" refers to derivatives of the compounds disclosed herein wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-l-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt may be 1:1, or any ratio other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

Salts of the compounds of formulas (IIa) and (IIb) according to the disclosure can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

According to the person skilled in the art the compounds of formulas (IIa) through (IIb) according to this disclosure as well as their salts may contain, e.g., when isolated in crystalline form, varying amounts of solvents. Included within the scope of the disclosure are therefore all solvates and in particular all hydrates of the compounds of formulas (IIa) through (IIb) according to this disclosure as well as all solvates and in particular all hydrates of the salts of the compounds of formulas (IIa) through (IIb) according to this disclosure.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The compounds according to the disclosure and their salts can exist in the form of tautomers which are included in the embodiments of the disclosure.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism.

Where the present specification depicts a compound prone to tautomerization, but only depicts one of the tautomers, it is understood that all tautomers are included as part of the meaning of the chemical depicted. It is to be understood that the compounds disclosed herein may be depicted as different tautomers. It should also be understood that when compounds have tautomeric forms, all tautomeric forms are intended to be included, and the naming of the compounds does not exclude any tautomer form.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

The compounds of the disclosure may, depending on their structure, exist in different stereoisomeric forms. These forms include configurational isomers or optically conformational isomers (enantiomers and/or diastereoisomers including those of atropisomers). The present disclosure therefore includes enantiomers, diastereoisomers as well as mixtures thereof. From those mixtures of enantiomers and/or disastereoisomers pure stereoisomeric forms can be isolated with methods known in the art, preferably methods of chromatography, especially high performance liquid chromatography (HPLC) using achiral or chiral phase. The disclosure further includes all mixtures of the stereoisomers mentioned above independent of the ratio, including the racemates.

The compounds of the disclosure may, depending on their structure, exist in various stable isotopic forms. These forms include those in which one or more hydrogen atoms have been replaced with deuterium atoms, those in which one or more nitrogen atoms have been replaced with $^{15}$N atoms, or those in which one or more atoms of carbon, fluorine, chlorine, bromine, sulfur, or oxygen have been replaced by the stable isotope of the respective, original atoms.

Some of the compounds and salts according to the disclosure may exist in different crystalline forms (polymorphs) which are within the scope of the disclosure.

It is a further object of the disclosure to provide protein kinase RPS6K1 inhibitor compounds disclosed herein, methods of synthesizing the protein kinase inhibitor compounds, methods of manufacturing the protein kinase inhibitor compounds, and methods of using the protein kinase inhibitor compounds. The compounds can also be made by synthetic schemes well established in the art.

Another object of the disclosure is to provide a composition, for example a pharmaceutical composition, comprising at least one protein kinase inhibitor compound disclosed herein in an amount effective for the indication of proliferative diseases such as cancer, including but not limited to breast cancer, prostate cancer, lung cancer, metastatic cancer, or solid tumors, etc. In an embodiment, the cancer is an ER-positive tumor and/or a HER2-positive tumor, such as a tumor of the breast, endometrium, uterus, or ovary. In an embodiment, the tumor is an ER-positive and/or HER2-positive tumor of the breast. In an embodiment, the tumor is a tumor of the prostate.

In an embodiment, the object of such treatment is to inhibit protein kinases, especially RPS6K1.

As used herein, "treating" means administering to a subject a pharmaceutical composition to ameliorate, reduce or lessen the symptoms of a disease. As used herein, "treating" or "treat" describes the management and care of a subject for the purpose of combating a disease, condition, or disorder and includes the administration of a compound disclosed herein, or a pharmaceutically acceptable salt, polymorph or solvate thereof, to alleviate the symptoms or complications of a disease, condition or disorder, or to eliminate the disease, condition or disorder. The term "treat" may also include treatment of a cell in vitro or an animal model. As used herein, "subject" or "subjects" refers to any animal, such as mammals including rodents (e.g., mice or rats), dogs, primates, lemurs or humans.

Treating cancer may result in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer may result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer may result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer may result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in increase in average survival time of a population of treated subjects in comparison to a population receiving monotherapy with a drug that is not a compound disclosed herein, or a pharmaceutically acceptable salt thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in a decrease in the mortality rate of a population of treated subjects in comparison to a population receiving carrier alone. Treating cancer may result in a decrease in the mortality rate of a population of treated subjects in comparison to an untreated population. Treating cancer may result in a decrease in the mortality rate of a population of treated subjects in comparison to a population receiving monotherapy with a drug that is not a compound disclosed herein, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer may result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate may be measured according to a change in tumor diameter per unit time.

Treating cancer may result in a decrease in tumor regrowth, for example, following attempts to remove it surgically. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder may result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder may result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells may be equivalent to the mitotic index.

Treating or preventing a cell proliferative disorder may result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder may result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology may be measured by microscopy, e.g., using an inverted tissue culture microscope. An abnormal cellular morphology may take the form of nuclear pleiomorphism.

As used herein, "subject" or "subjects" refers to any animal, such as a warm-blooded animal, i.e., mammals including rodents (e.g., mice or rats), dogs, primates, lemurs or humans.

EXAMPLES

Hereby are provided non-limiting examples of embodiments of compounds disclosed herein.

Derivative compounds having the core structure isoindoline-1,3-dione (formula (Ia)) were synthesized.

We identified 4,6-diaminoisoindoline-1,3-dione (RJ1) (RPS6KB1 (p70S6K), formula (Ib)) as a RPS6K1-selective inhibitor when tested against a panel of 120 disease relevant kinases (Table 1) using the SelectScreen™ Biochemical Kinase Profiling Service. The complete list of the kinases given in Table 1 and their details can be found on the ThermoFisher website for Biochemical Kinase assays (thermofisher.com/us/en/home/industrial/pharma-biopharma/drug-discovery-development/target-and-lead-identification-and-validation/kinasebiology.html).

TABLE 1

High-throughput screening of 4,6-diaminoisoindoline-1,3-dione against a panel of disease relevant human kinases

| Kinase | % Inhibition | |
|---|---|---|
| CDK7/cyclin H/MNAT1 | −1 | * |
| CDK9/cyclin T1 | 16 | * |
| GSG2 (Haspin) | 65 | ** |
| PIK3CA/PIK3R1 (p110 alpha/p85 alpha) | 23 | * |
| PIK3CG (p110 gamma) | 12 | * |
| SPHK1 | 23 | * |
| CDK7/cyclin H/MNAT1 | 1 | * |
| CDK9/cyclin T1 | 10 | * |
| GSG2 (Haspin) | 34 | * |
| PIK3CA/PIK3R1 (p110 alpha/p85 alpha) | 3 | * |
| PIK3CG (p110 gamma) | 11 | * |
| SPHK1 | 53 | ** |
| ABL1 | 59 | ** |
| ABL2 (Arg) | 54 | ** |
| AKT1 (PKB alpha) | 11 | * |
| AKT2 (PKB beta) | 9 | * |
| ALK | 32 | * |
| AURKA (Aurora A) | 43 | ** |
| AURKB (Aurora B) | 63 | ** |
| AURKC (Aurora C) | 40 | * |
| AXL | 10 | * |
| BRAF V599E | 22 | * |
| BRAF | 19 | * |
| BTK | 43 | ** |
| CDC42 BPA (MRCKA) | 0 | * |
| CDC42 BPB (MRCKB) | 0 | * |
| CDK1/cyclin B | 8 | * |
| CDK2/cyclin A | 9 | * |
| CDK5/p25 | 27 | * |
| CHEK1 (CHK1) | 72 | ** |
| CHEK2 (CHK2) | 38 | * |
| CSF1R (FMS) | 26 | * |
| CSNK1E (CK1 epsilon) | 33 | * |
| CSNK2A1 (CK2 alpha 1) | 5 | * |
| EGFR (ErbB1) | 12 | * |
| EPHA1 | 15 | * |
| EPHA2 | 16 | * |
| EPHB2 | 10 | * |
| EPHB4 | 9 | * |
| ERBB2 (HER2) | 6 | * |
| ERBB4 (HER4) | 25 | * |
| FER | 23 | * |
| FES (FPS) | 36 | * |
| FGFR1 | 51 | ** |
| FGFR4 | 20 | * |
| FGR | 51 | ** |
| FLT1 (VEGFR1) | 18 | * |
| FLT3 | 29 | * |
| FLT4 (VEGFR3) | 55 | ** |
| FRAP1 (mTOR) | 6 | * |
| FYN | 17 | * |
| HCK | 21 | * |
| IGF1R | 10 | * |
| IKBKB (IKK beta) | 16 | * |
| IKBKE (IKK epsilon) | 16 | * |
| JAK1 | 9 | * |
| JAK2 JH1 JH2 V617F | 6 | * |
| JAK2 JH1 JH2 | 15 | * |
| JAK2 | 22 | * |
| JAK3 | 28 | * |
| KDR (VEGFR2) | 56 | ** |
| KIT | 7 | * |
| LCK | 31 | * |
| LYN A | 12 | * |
| MAP2K1 (MEK1) | 13 | * |
| MAP3K8 (COT) | 29 | * |
| MAP4K4 (HGK) | 66 | ** |
| MAPK14 (p38 alpha) Direct | 2 | * |
| MATK (HYL) | −5 | * |
| MET (cMet) | −4 | * |
| MST1R (RON) | 27 | * |
| MST4 | 52 | ** |
| NEK2 | −20 | * |
| NTRK1 (TRKA) | 5 | * |
| PAK4 | 29 | * |
| PDGFRA (PDGFR alpha) | 13 | * |
| PDGFRB (PDGFR beta) | 5 | * |
| PDK1 Direct | 33 | * |
| PIM1 | 35 | * |
| PLK1 | 9 | * |
| PLK3 | 77 | ** |
| PRKCB2 (PKC beta II) | 23 | * |
| PTK2 (FAK) | 26 | * |
| PTK2B (FAK2) | 18 | * |
| PTK6 (Brk) | 4 | * |
| RAF1 (cRAF) Y340D Y341D | 6 | * |
| RET | 79 | ** |
| ROCK1 | 21 | * |
| ROS1 | 3 | * |
| RPS6KB1 (p70S6K) | 80 | *** |
| SGK (SGK1) | 50 | ** |
| SRC | 9 | * |
| SYK | 39 | * |
| TBK1 | 18 | * |
| TEK (Tie2) | 20 | * |
| TYRO3 (RSE) | 25 | * |
| YES1 | 24 | * |

Legend
<40% Inhibition       *
40%-80% Inhibition   **
≥80% Inhibition      ***

The compound (RPS6KB1 (p70S6K), denoted RJ1) showed 80% inhibition of the kinase at a concentration of 10 μM. RJ1 was taken as the lead structure for the synthesis of several diamide and monoamide derivatives of 4,6-diaminoisoindolin-1,3-dione.

Figure 2:
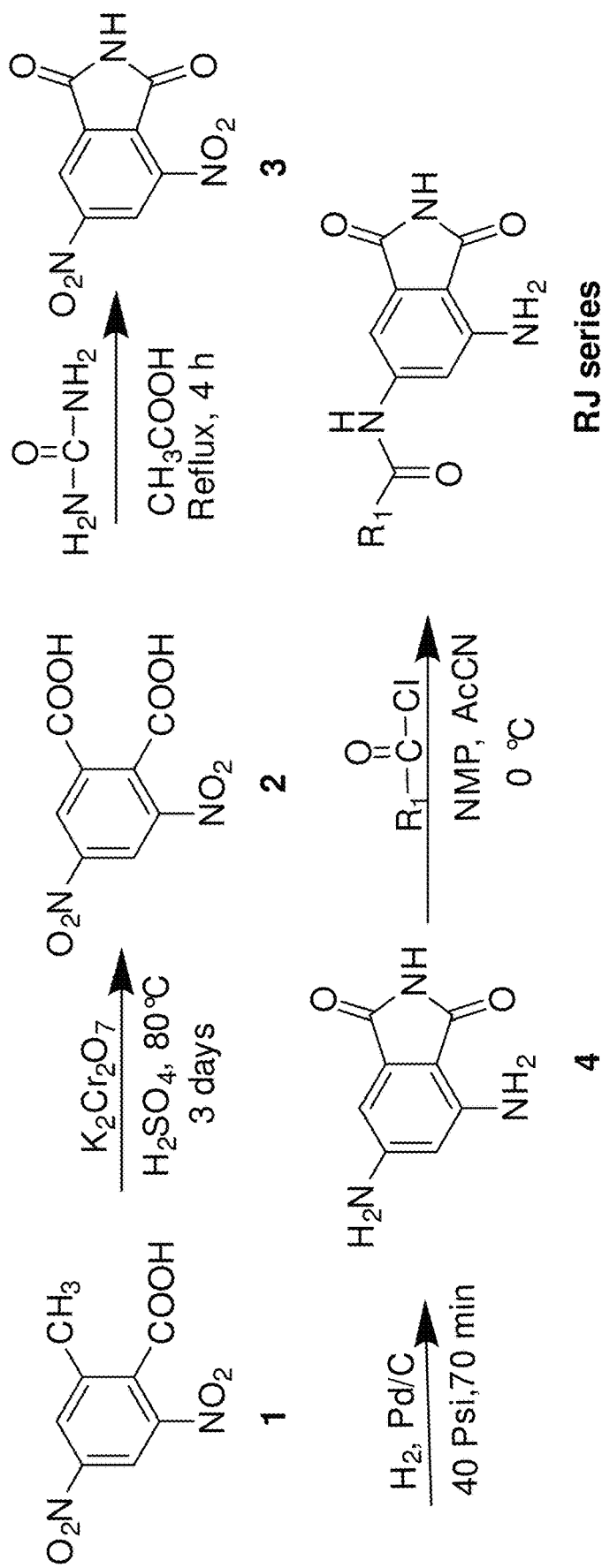
FIG. 2 shows synthetic scheme for the synthesis of 4-amino-6-amidoisoindoline-1,3-dione derivatives.

A. Synthesis of various 4,6-diaminoisoindolin-1,3-dione/4-amino-6-amidoisoindoline-1,3-dione derivatives FIG. 2 shows steps of synthesis for various 4-amino-6-amidoisoindoline-1,3-dione derivatives.

Experimental Methods:

All reagents were used as received from the manufacturer, with the exception of (N-Bromosuccinimide), which was recrystallized from water and allowed to dry before use. All NMR spectra were recorded with an Agilent 400 MHz NMR magnet using tetramethylsilane as an internal solvent reference. Aluminum backed 60F254 silica plates were used for thin-layer chromatography. Flash chromatography was performed using a Teledyne Isco CombiFlash automated column machine with ethyl acetate and hexane as the mobile solvents.

Synthesis of 3,5-dinitrophthalic acid (2): To a stirring solution of 4,6-dinitrotoluic acid (1) (25 g, 0.111 mol) in 200 mL of sulfuric acid at 80° C. was added potassium dichromate (65.014, 0.222 mol) in portions keeping the reaction temperature below 90° C. After completion of the addition, stirring of the resulting reaction mixture continued at 80° C. for 2 days. Upon completion, the reaction mixture was cooled down to room temperature and the reaction mixture was poured into an ice+water mixture. Extraction was performed with diethyl ether and concentrate under reduced pressure to get a slightly yellowish solid, which contains both product and starting material. To purify, the mixture was heated to 80° C. with 100 mL of benzene for 15 min. and decanted while hot. The benzene wash was performed multiple times (at least twice), and purity was verified by NMR. (31).

Synthesis of 4,6-dinitroisoindoline-1,3-dione (3): To a stirring solution of 3,5-dinitrophthalic acid (2) (2.56 g, 10.0 mmol) in 20 mL of acetic acid was added urea (1.20 g, 20 mmol) and refluxed for 4 h. After completion of 4 h, the reaction mixture was cooled to room temperature, poured onto ice, and stirred. The obtained precipitate was filtered, washed with water and dried under vacuum to get the product 4,6-dinitroisoindoline-1,3-dione (3) in 76% yield. (32).

Synthesis of 4,6-diaminoisoindoline-1,3-dione (4): Pd/C (10mg) was added to 4,6-dinitroisoindoline-1,3-dione (0.024 g, 0.1 mmol) in methanol and subjected to hydrogenation in a Parr Shaker at a $H_2$ pressure of 40 psi for 70 minutes. Upon completion, the reaction was filtered through celite and concentrated to obtain the product as a dirty green solid with over 90% yield. $H^1$ NMR: 10.3 (s, 1H), 6.19 (S, 1H), 6.01 (s, 2H), 5.96 (s, 2H), 5.90 (s, 1H)

General method to synthesis of monoamido pthalimide derivatives (5—RJ Series of compounds): A solution of acyl chloride (0.173 mmol) in 3 ml of acetonitrile was added, dropwise, to a stirring solution of 4,6-diaminoisoindoline-1,3-dione (4) (0.0231 g, 0.173 mmol) in 2 ml of N-methyl-2-pyrrolidone at 0° C. The resulting solution was stirred at 0° about corresponding time (refer to table), after completion reaction mixture was poured into ice+water. Resulted precipitate was filtered off and washed with water for several time and dried under vacuum to get the corresponding product.

TABLE 2

| Compound ID | Acyl Chloride | Product Structure | Reaction time | Isolated Yield |
|---|---|---|---|---|
| RJ-19 | (benzoyl chloride) | (benzamide-diaminoisoindolinedione) | 5 min | 81.6% |
| RJ-20 | (4-cyanobenzoyl chloride) | (4-cyanobenzamide derivative) | 3 min | 86.4% |
| RJ-21 | (5-chlorothiophene-2-carbonyl chloride) | (5-chlorothiophene-2-carboxamide derivative) | 1 h | 91.7% |
| RJ-22 | (2-bromobenzoyl chloride) | (2-bromobenzamide derivative) | 4 h | 80.6% |
| RJ-23 | (3-bromobenzoyl chloride) | (3-bromobenzamide derivative) | 8 min | 87.5% |
| RJ-24 | (4-bromobenzoyl chloride) | (4-bromobenzamide derivative) | 8 min | 83.4% |

TABLE 2-continued

| Compound ID | Acyl Chloride | Product Structure | Reaction time | Isolated Yield |
|---|---|---|---|---|
| RJ-25 | | | 1 h at 0° C. + 4 h at RT | 68.9% |
| RJ-26 | | | 3 min | 98.3% |
| RJ-27 | | | 6 min | 97.5% |
| RJ-28 | | | 1 min | 63.5% |

NMR Data:

RJ-19: ¹HNMR: δ 10.79 (s, 1H), 10.45 (s, 1H), 7.92 (d, 2H, J=4 Hz), 7.59-7.50 (m, 4H), 7.34 (s, 1H), 6.40 (b, 2H) ppm; ¹³C NMR: δ 170.9, 169.7, 166.5, 147.6, 145.7, 134.9, 132.3, 128.9, 128.3, 110.2, 106.2, 106.4, 104.23 ppm.

RJ-20: ¹H NMR: δ 10.82(s, 1H), 10.66 (s, 1H), 8.07 (d, 2H, J=12 Hz), 8.01 (d, 2H, J=8 Hz), 7.52 (s, 1H), 7.32 (s, 1H), 6.44 (b, 2H) ppm; ¹³C NMR: δ170.85, 169.61, 165.14, 147.56, 145.27, 138.99, 134.91, 132.94, 129.12, 118.71, 114.53, 110.41, 106.70, 104.10 ppm.

RJ-21: ¹HNMR: δ 10.81(s, 1H), 10.45 (s, 1H), 7.93 (d, 1H, J=4 Hz), 7.40 (d, 1H, J=4 Hz), 7.27 (d, 2H, J=8 Hz), 6.43 (b, 2H) ppm; ¹³C NMR: δ 170.84, 169.59,159.55, 147.51, 144.97, 138.96, 135.07, 134.95, 130.23, 128.79, 110.22, 106.64, 103.96 ppm.

RJ-22: ¹H NMR: 10.81 (s, 1H), 10.75 (s, 1H), 7.71 (d, 1H, J=4 Hz), 7.42-7.54 (m, 4H), 7.19 (s, 1H), 6.43 (b, 2H); ¹³C NMR: 170.87, 169.58, 166.71, 147.67, 145.28, 139.11, 135.04, 133.18, 131.87, 129.29, 128.22, 119.35, 104.73, 106.59, 103.46 ppm.

RJ-23: ¹HNMR: δ 10.82 (s, 1H), 10.53 (s, 1H), 8.09 (s, 1H), 7.91 (d, 1H, J=8 Hz), 7.79 (d, 1H, J=8 Hz), 7.49 (d, 2H, J=8 Hz), 7.30 (s, 1H), 6.40 (b, 2H); ¹³C NMR: δ 170.88, 169.64, 164,89, 147.54, 145.42, 137.08, 135.02, 134.86, 131.10, 130.79, 127.46, 122.12, 110.37, 106.59, 104.21 ppm.

RJ-24: ¹HNMR: δ 10.80 (s, 1H), 10.50 (s, 1H), 7.87 (d, 2 H, J=12 Hz), 7.73 (d, 2H, J=8 Hz), 7.51 (s, 1H), 7.31 (s, 1H), 6.41 (b, 2H) ppm; ¹³C NMR: δ 170.88, 169.65, 165.49, 147.55, 145.52, 134.87, 133.99, 131.88, 130.38, 126.16, 110.30, 106.52, 104.18 ppm.

RJ-25: ¹H NMR: δ 11.04 (s, 1H), 10.84 (s, 1H), 7.41 (s, 1H), 7.25(t, 3H, J=8 Hz), 7.16 (s, 1H), 6.46 (b, 2H) ppm;

¹³CNMR: δ 170.81, 169.48, 160.43, 159.0, 157.96, 147.71, 144.70, 135.2, 132.88, 115.67, 115.23, 112.73, 109.66, 106.96, 103.03 ppm.

RJ-26: ¹HNMR: δ 10.82(s, 1H), 10.53 (s, 1H), 8.09 (s, 1H), 7.91(d, 1 H, J=8 Hz), 7.79 (d, 1H, J=8 Hz), 7.49 (d, 2H, J=8 Hz), 7.30 (s, 1H), 6.60 (b, 2H) ppm; ¹³CNMR: 170.86, 169.61, 164.25, 148.13, 147.54, 145.22, 136.28, 134.90, 134.77, 130.66, 126.87, 123.00, 110.54, 106.74, 104.20 ppm.

RJ-27: ¹HNMR: δ 10.83(s, 1H), 10.74(s, 1H), 8.35(d, 2H, J=8 Hz), 8.15 (d, 2H, J=8 Hz), 7.52 (s, 1H), 7.32 (s, 1H), 6.45 (b, 2H) ppm; ¹³C NMR: δ 170.85, 169.59, 164.84, 149.70, 147.54, 145.21, 140.57, 134.91, 129.80, 123.99, 110.46, 106.76, 104.11

RJ-28: ¹HNMR: δ 10.98 (s, 1H), 10.86 (s, 1H), 9.13 (s, 2H), 9.00 (s, 1H), 7.51 (s, 1H), 7.34 (s, 1H), 6.49 (b, 2H) ppm; ¹³C NMR: δ 170.78, 169.50, 162.09, 148.45, 147.48, 144.76, 137.38, 134.87, 128.57, 121.72, 110.69, 106.95, 104.13 ppm.

General Procedure for the synthesis of RJ-29, RJ-30 and RJ-31:

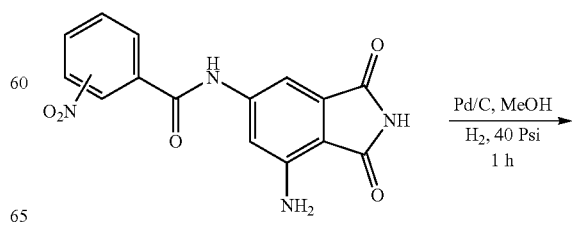

RJ-26; RJ-27; RJ-28

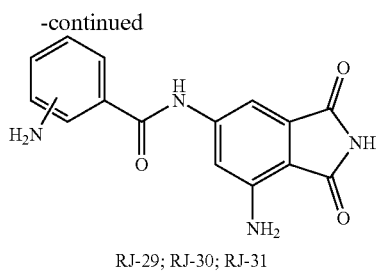

RJ-29; RJ-30; RJ-31

Pd/C (10 mg) was added to N-(7-amino-1,3-dioxoisoindolin-5-yl)-3-nitrobenzamide (RJ-26) (0.033 g, 0.1 mmol) in methanol and subjected to hydrogenation in a Parr Shaker at a $H_2$ pressure of 40 psi for 1 h. Upon completion, the reaction was filtered through celite and concentrated to obtain the product 3-amino-N-(7-amino-1,3-dioxoisoindolin-5-yl)benzamide (6a) with an isolated yield 93.2%. A similar procedure was followed for the conversion of RJ-27 and RJ-28 to RJ-30 and RJ-31, respectively.

TABLE 3

| Compound ID | Product Structure | Isolated Yield |
|---|---|---|
| RJ-29 | | 93.2% |
| RJ-30 | H₂N–C₆H₄–C(O)NH–isoindoline-1,3-dione-NH₂ | 91.7% |
| RJ-31 | (NH₂)(H₂N)–C₆H₃–C(O)NH–isoindoline-1,3-dione-NH₂ | 94.5% |

NMR Data:

General Procedure for the synthesis of RJ-29, RJ-30 and RJ-31:

RJ-29: $^1$HNMR: δ 10.76 (b, 1H), 10.30 (s, 1H), 7.53 (s, 1H), 7.30 (s, 1H), 7.13 (t, 2H, J=8 Hz), 7.02 (d, 1H, J=12 Hz), 6.73 (d, 2H, J=4 Hz), 6.37 (s, 1H), 5.33 (b, 2H) ppm; $^{13}$CNMR: 170.91, 169.72, 167.32, 149.25, 147.56, 145.95, 135.93, 134.81, 129.27, 117.53, 115.27, 113.40, 110.05, 106.18, 104.20 ppm.

RJ-30: $^1$HNMR: δ 10.72 (b, 1H), 9.97 (s, 1H), 7.69 (d, 2H, J=8 Hz), 7.52 (s, 1H), 7.32 (s, 1H), 6.57 (d, 2H, J=8 Hz), 6.33 (s, 2H), 5.83 (s, 2H) ppm; $^{13}$C NMR: δ 170.92, 169.79, 166.06, 152.97, 147.55, 146.45, 134.75, 130.08, 120.83, 112.94, 104.70, 105.74, 104.20

RJ-31: $^1$HNMR: δ 10.74 (b, 1H), 10.20 (s, 1H), 7.52 (s, 1H), 7.26 (s, 1H), 6.34 (s, 2H), 6.24 (s, 2H), 5.98 (s, 1H), 4.96 (s, 4H) ppm; $^{13}$CNMR: 6170.91, 169.74, 168.23, 149.63, 147.56, 146.18, 144.50, 136.80, 134.78, 109.81, 105.96, 104.13, 102.87, 102.73 ppm.

Cell viability assays used the methods outlined in an earlier publication: Identification of New Mono/Dihydroxynaphthoquinone as Lead Agents that Inhibit the Growth of Refractive and Triple-negative Breast Cancer Cell lines. Schroeder, R.; Sfondouris, M.; Goyal, N.; Komati, R.; Weerathunga, A.; Gettridge, C.; Stevens, C. L. K.; Jones, F. E.; Sridhar, J. ACS Omega, 2019 Jun 19. 4(6):10610-10619.

B. Inhibitory Activity of the various 4,6-diaminoisoindolin-1,3-dione/4-amino-6-amidoisoindoline-1,3-dione derivatives The 4-amino-6-amidoisoindolin-1,3-diones were found to inhibit RPS6K1 with a range of 27% to 86% at a 10 μM concentration (Table 4).

TABLE 4

High-throughput screening of the 4-amino-6-amidoisoindoline-1,3-dione compounds for the for the inhibition of RPS6K1.

| Compound | RPS6K1% inhibition at 10 mM compound concentration |
|---|---|
| RJ-7 | 50 |
| RJ-19 | 71 |
| RJ-20 | 27 |
| RJ-21 | 37 |
| RJ-22 | 86 |
| RJ-23 | 40 |
| RJ-24 | 40 |
| RJ-25 | 38 |
| RJ-26 | 50 |
| RJ-27 | 65 |
| RJ-28 | 79 |
| RJ-29 | 65 |
| RJ-30 | 64 |
| RJ-31 | 58 |

As seen from Table 4, three of the compounds RJ19, RJ22 and RJ28 were found to exhibit >70% inhibition of the kinase in the high-throughput screening. These three compounds were then subjected to $IC_{50}$ value determination (dose response curve) using the same FRET based assay by ThermoFisher (Table 5). RJ-2 was determined to be selective for two other kinases (WEE1 and PLK3) (not shown in Table). It also selectively inhibited CK1epsilon (70%) over CK1delta (30%).

TABLE 5

$IC_{50}$ values of inhibition of RPS6K1 for the compounds RJ-19, RJ-22 and RJ-28.

| Compound | $IC_{50}$ value of inhibition of RPS6K1 in μM |
|---|---|
| RJ-28 | 2.56 |
| RJ-22 | >2.78 |
| RJ-19 | 3.48 |

As shown by Table 5, the $IC_{50}$ values of inhibition for RJ19, RJ22 and RJ28 were 3.48 μM, >2.78 μM and 2.56 μM, respectively.

RPS6K1 is known to play a critical role in several cancers including HER2 positive breast cancer, ER positive breast cancer, prostate cancer and small cell lung cancer. To verify whether RPS6K1 inhibitors of the instant disclosure could inhibit growth of these types of cancers, MTT assays were performed using the HER2 positive breast cancer cell line SKBR3, ER positive breast cancer cell line MCF7, and the prostate cancer cell line DU-145. The MTT assay is a colorimetric assay for assessing cell metabolic activity. NAD(P)H-dependent cellular oxidoreductase enzymes may, under defined conditions, reflect the number of viable cells present. These enzymes are capable of reducing the tetrazolium dye MTT 3-(4,5-dimethylthiazol-2-yl)-2,5-diphenyltetrazolium bromide to its insoluble formazan, which has a purple color. RJ22 and RJ28 showed excellent growth inhibition of all three cell lines in the low micromolar range (FIGS. 1A, 1B and 1C). RJ19 showed inhibition of the HER2 positive breast cancer cell line SKBR3, but was not as effective for the ER positive breast cancer cell line MCF7 (FIGS. 1A and 1B). The $IC_{50}$ values of growth inhibition of the SKR3 breast cancer cell line for all three compounds RJ19, RJ22 and RJ28 was determined to be 3.3 µM, 1.9 µM and 4.7 µM, respectively.

Figure 3:
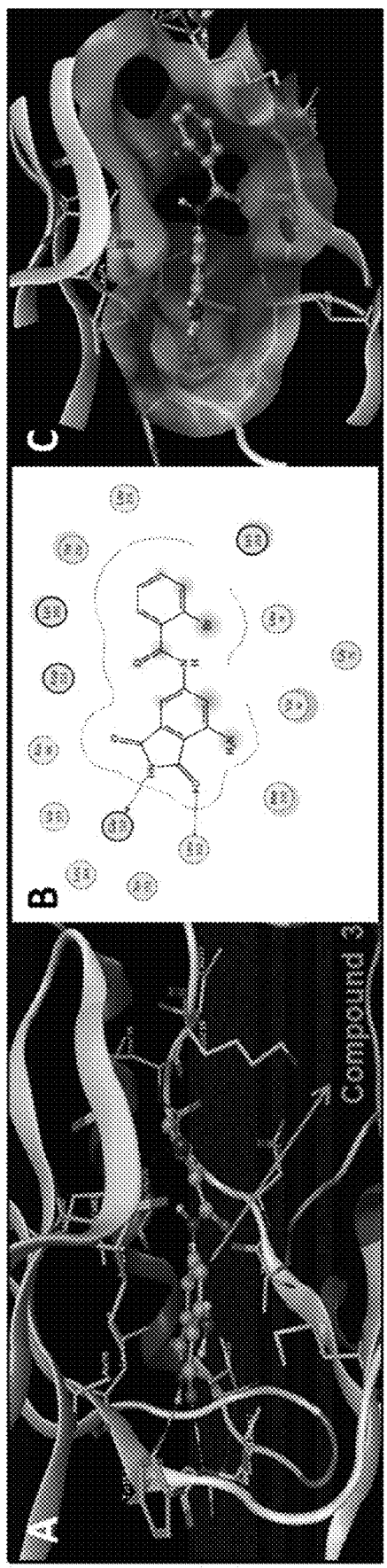
FIG. 3 shows docking of RJ22 in the ATP-binding pocket of S6K1 protein. (A) shows 3D-depiction of the binding mode of RJ22 is shown and the hydrogen bonds with Glu150 and Leu152 are depicted with borken cyan lines; (B) shows 2D-depiction of the interaction of RJ22 with S6K1 binding pocket residues; and (C) the surface mapping of the binding pocket aournd the inhibitor showing the coverage of RJ22 in the pocket.

To understand the nature of binding of these compounds to the ATP-binding pocket of the RPS6K1 protein (4L3J.pdb), docking studies were performed using the molecular modeling software MOE (CHEMCOMP Group). We found that a carbonyl and the NH of the phthalimide core structure formed hydrogen bonds with the hinge region residues Glu150 and Leu152 (FIG. 3). An aromatic π-methyl interaction was found to occur between the phenyl ring of phthalimide and the binding cavity residue Val82. The 6-amido carbonyl group was within hydrogen bonding distance of the side chain hydroxyl group of residue Thr212.

Thus, this demonstrates that a new class of compounds has been identified, and that these compounds are selective inhibitors of RPS6K1 protein. These compounds show growth inhibition of several cancer cell lines including HER2 positive breast cancer, ER positive breast cancer and prostate cancer cell lines. These compounds can serve as therapeutics for any type of cancer where the AKT/mTOR signaling pathway is upregulated.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

REFERENCES CITED

1. American Cancer Society. Cancer Facts & Figures 2019. Atlanta: *American Chemical Society* 2019.
2. Amaral, C. L.; Freitas, L. B.; Tamura, R. E.; Tavares, M. R.; Pavan, I. C.; Bajgelman, M. C.; Simabuco, F. M., S6Ks isoforms contribute to viability, migration, docetaxel resistance and tumor formation of prostate cancer cells. *BMC Cancer* 2016, 16, 602.
3. Zhang, Y.; Ni, H. J.; Cheng, D. Y., Prognostic value of phosphorylated mTOR/RPS6KB1 in non- small cell lung cancer. *Asian PacJ Cancer Prev* 2013, 14 (6), 3725-8.
4. Wang, D.; Chen, J.; Guo, F.; Chen, H.; Duan, Z.; Wei, M. Y.; Xu, Q. M.; Wang, L. H.; Zhong, M. Z., Clinical significance of mTOR and p-mTOR protein expression in human colorectal carcinomas. *Asian PacJ Cancer Prev* 2011, 12 (10), 2581-4.
5. Chen, J.; Fang, Y., A novel pathway regulating the mammalian target of rapamycin (mTOR) signaling. *Biochem Pharmacol* 2002, 64 (7), 1071-7.
6. Bahrami, B. F.; Ataie-Kachoie, P.; Pourgholami, M. H.; Morris, D. L., p70 Ribosomal protein S6 kinase (Rps6kb1): an update. *J Clin Pathol* 2014, 67 (12), 1019-25.
7. Holz, M. K., The role of S6K1 in ER-positive breast cancer. *Cell Cycle* 2012, 11 (17), 3159-65.
8. Holz, M. K.; Ballif, B. A.; Gygi, S. P.; Blenis, J., mTOR and S6K1 mediate assembly of the translation preinitiation complex through dynamic protein interchange and ordered phosphorylation events. *Cell* 2005, 123 (4), 569-80.
9. Shahbazian, D.; Roux, P. P.; Mieulet, V.; Cohen, M. S.; Raught, B.; Taunton, J.; Hershey, J. W.; Blenis, J.; Pende, M.; Sonenberg, N., The mTOR/P13K and MAPK pathways converge on eIF4B to control its phosphorylation and activity. *EMBO J* 2006, 25 (12), 2781-91.
10. Cai, C.; Chen, Q. B.; Han, Z. D.; Zhang, Y. Q.; He, H. C.; Chen, J. H.; Chen, Y. R.; Yang, S. B.; Wu, Y. D.; Zeng, Y. R.; Qin, G. Q.; Liang, Y. X.; Dai, Q. S.; Jiang, F. N.; Wu, S. L.; Zeng, G. H.; Zhong, W. D.; Wu, C. L., miR-195 Inhibits Tumor Progression by Targeting RPS6KB1 in Human Prostate Cancer. *Clin Cancer Res* 2015, 21 (21), 4922-34.
11. Chen, B.; Yang, L.; Zhang, R.; Gan, Y.; Zhang, W.; Liu, D.; Chen, H.; Tang, H., Hyperphosphorylation of RPS6KB1, rather than overexpression, predicts worse prognosis in non-small cell lung cancer patients. *PLoS One* 2017, 12 (8), e0182891.
12. Ismail, H. M., Overexpression of s6 kinase 1 in brain tumours is associated with induction of hypoxia-responsive genes and predicts patients' survival. *J Oncol* 2012, 2012, 416927.
13. Karlsson, E.; Magic, I.; Bostner, J.; Dyrager, C.; Lysholm, F.; Hallbeck, A. L.; Stal, 0.; Lundstrom, P., Revealing Different Roles of the mTOR-Targets S6K1 and S6K2 in Breast Cancer by Expression Profiling and Structural Analysis. *PLoS One* 2015, 10 (12), e0145013.
14. van der Hage, J. A.; van den Broek, L. J.; Legrand, C.; Clahsen, P. C.; Bosch, C. J.; Robanus-Maandag, E. C.; van de Velde, C. J.; van de Vijver, M. J., Overexpression of P70 S6 kinase protein is associated with increased risk of locoregional recurrence in node-negative premenopausal early breast cancer patients. *Br J Cancer* 2004, 90 (8), 1543-50.
15. Zhang, S.; Hu, B.; Lv, X.; Chen, S.; Liu, W.; Shao, Z., The Prognostic Role of Ribosomal Protein S6 Kinase 1 Pathway in Patients With Solid Tumors: A Meta-Analysis. *Front Oncol* 2019, 9, 390.
16. Aronchik, I.; Appleton, B. A.; Basham, S. E.; Crawford, K.; Del Rosario, M.; Doyle, L. V.; Estacio, W. F.; Lan, J.; Lindvall, M. K.; Luu, C. A.; Ornelas, E.; Venetsanakos, E.; Shafer, C. M.; Jefferson, A. B., Novel potent and selective inhibitors of p90 ribosomal S6 kinase reveal the heterogeneity of RSK function in MAPK-driven cancers. *Mol Cancer Res* 2014, 12 (5), 803-12.
17. Yamnik, R. L.; Holz, M. K., mTOR/S6K1 and MAPK/RSK signaling pathways coordinately regulate estrogen receptor alpha serine 167 phosphorylation. *FEBS Lett* 2010, 584 (1), 124-8.
18. Fingar, D. C.; Richardson, C. J.; Tee, A. R.; Cheatham, L.; Tsou, C.; Blenis, J., mTOR controls cell cycle progression through its cell growth effectors S6K1 and 4E-BP1/eukaryotic translation initiation factor 4E. *Mol Cell Bio!* 2004, 24 (1), 200-16.

19. Lane, H. A.; Fernandez, A.; Lamb, N. J.; Thomas, G., p70s6k function is essential for G1 progression. *Nature* 1993, 363 (6425), 170-2.
20. Yamnik, R. L.; Digilova, A.; Davis, D. C.; Brodt, Z. N.; Murphy, C. J.; Holz, M. K., S6 kinase 1 regulates estrogen receptor alpha in control of breast cancer cell proliferation. *J Biol Chem* 2009, 284 (10), 6361-9.
21. Chappell, W. H.; Steelman, L. S.; Long, J. M.; Kempf, R. C.; Abrams, S. L.; Franklin, R. A.; Basecke, J.; Stivala, F.; Donia, M.; Fagone, P.; Malaponte, G.; Mazzarino, M. C.; Nicoletti, F.; Libra, M.; Maksimovic-Ivanic, D.; Mijatovic, S.; Montalto, G.; Cervello, M.; Laidler, P.; Milella, M.; Tafuri, A.; Bonati, A.; Evangelisti, C.; Cocco, L.; Martelli, A. M.; McCubrey, J. A., Ras/Raf/MEK/ERK and PI3K/PTEN/Akt/mTOR inhibitors: rationale and importance to inhibiting these pathways in human health. *Oncotarget* 2011, 2 (3), 135-64.
22. Steelman, L. S.; Chappell, W. H.; Abrams, S. L.; Kempf, R. C.; Long, J.; Laidler, P.; Mijatovic, S.; Maksimovic-Ivanic, D.; Stivala, F.; Mazzarino, M. C.; Donia, M.; Fagone, P.; Malaponte, G.; Nicoletti, F.; Libra, M.; Milella, M.; Tafuri, A.; Bonati, A.; Basecke, J.; Cocco, L.; Evangelisti, C.; Martelli, A. M.; Montalto, G.; Cervello, M.; McCubrey, J. A., Roles of the Raf/MEK/ERK and PI3K/PTEN/Akt/mTOR pathways in controlling growth and sensitivity to therapy-implications for cancer and aging. *Aging* (Albany N.Y.) 2011, 3 (3), 192-222.
23. Couty, S.; Westwood, I. M.; Kalusa, A.; Cano, C.; Travers, J.; Boxall, K.; Chow, C. L.; Burns, S.; Schmitt, J.; Pickard, L.; Barillari, C.; McAndrew, P. C.; Clarke, P. A.; Linardopoulos, S.; Griffin, R. J.; Aherne, G. W.; Raynaud, F. I.; Workman, P.; Jones, K.; van Montfort, R. L., The discovery of potent ribosomal S6 kinase inhibitors by high-throughput screening and structure-guided drug design. *Oncotarget* 2013, 4 (10), 1647-61.
24. Neise, D.; Sohn, D.; Stefanski, A.; Goto, H.; Inagaki, M.; Wesselborg, S.; Budach, W.; Stuhler, K.; Janicke, R. U., The p90 ribosomal S6 kinase (RSK) inhibitor BI-D1870 prevents gamma irradiation-induced apoptosis and mediates senescence via RSK- and p53-independent accumulation of p21WAF1/CIP1. *Cell Death Dis* 2013, 4, e859.
25. Sapkota, G. P.; Cummings, L.; Newell, F. S.; Armstrong, C.; Bain, J.; Frodin, M.; Grauert, M.; Hoffmann, M.; Schnapp, G.; Steegmaier, M.; Cohen, P.; Alessi, D. R., BI-D1870 is a specific inhibitor of the 90 RSK (ribosomal S6 kinase) isoforms in vitro and in vivo. *Biochem J* 2007, 401 (1), 29-38.
26. Poleri C, Morero JL, Nieva B, Vazquez MF, Rodriguez C, De Titto E, et al. Risk of recurrence in patients with surgically resected stage I non-small cell lung carcinoma: histopathologic and immunohistochemical analysis. CHEST Journal. 2003; 123(6):1858±67.
27. Di Conza G, Cafarello ST, Loroch S, Mennerich D, Deschoemaeker S, Di Matteo M, et al. The mTOR and PP2A Pathways Regulate PHD2 Phosphorylation to Fine-Tune HIF1a Levels and Colorectal Cancer Cell Survival under Hypoxia. Cell Reports. 2017; 18(7):1699±712. https://doi.org/10.1016/j.celrep. 2017.01.051 PM ID: 28199842.
28. Fenton TR, Gout IT. Functions and regulation of the 70 kDa ribosomal S6 kinases. The international journal of biochemistry & cell biology. 2011; 43(1):47±59.
29. Shin S, Wolgamott L, Yu Y, Blenis J, Yoon S-O. Glycogen synthase kinase (GSK)-3 promotes p70 ribosomal protein S6 kinase (p70S6K) activity and cell proliferation. Proceedings of the National Academy of Sciences. 2011; 108(47):E1204±E13.
30. Dowling RJ, Topisirovic I, Fonseca BD, Sonenberg N (2010). Dissecting the role of mTOR: lessons from mTOR inhibitors. Biochim Biophys Acta 1804: 433-439).
31. Helvetica Chimica Acta, 68(4), 846-53; 1985).
32. Chattopadhyay, G.; Sinha, R. P. Hydrazine-Hydroquinone Complex as an Efficient Solid Phase Hydrazine Donor: High Yield Synthesis of Luminol and Isoluminol, J.Chem.Res, 35 (6), 326-328, 2011)

What is claimed is:

1. A compound according to formula (IIa) or formula (IIb), a stereoisomer, pharmaceutically acceptable salt and/or solvate thereof:

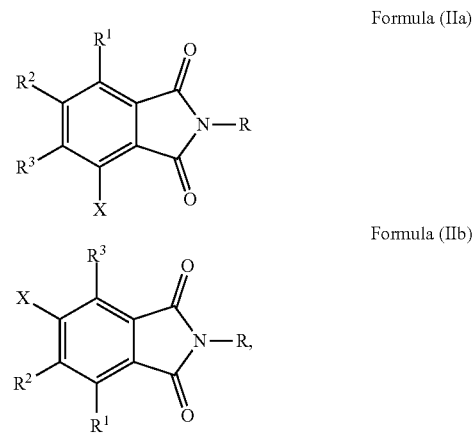

Formula (IIa)

Formula (IIb)

wherein
R is H;
X is —NH$_2$;
R$^1$ is NR$^5$COR$^5$;
R$^2$ and R$^3$ are each independently selected from the group consisting of H and NR$^5$COR$^5$;
R$^4$ is selected from the group consisting of H, halogen, C$_{1-6}$ alkyl, C$_{1-6}$ alkenyl, C$_{1-6}$ alkoxy, C$_{1-6}$ haloalkyl, haloC$_{1-6}$ alkoxy, —COOH, —CONH$_2$, —COC$_{1-6}$ alkyl, O—C$_{1-6}$ alkyl, NH—C$_{1-6}$ alkyl, —S C$_{1-6}$ alkyl groups, —CN, —NH$_2$, and —NO$_2$; and
R$^5$ is selected form the group consisting of H, aryl, C$_{3-8}$ cycloalkyl, monocyclic or bicyclic heterocyclyl, and monocyclic or bicyclic heteroaryl, wherein the aryl, heteroaryl or heterocyclyl groups may be optionally substituted by one or more R$^4$ groups.

2. The compound of formula (IIa) according to claim 1, wherein:
R is H; is H or alkyl;
X is NH$_2$;
R$^1$ is NR$^5$COR$^5$; is selected from the group consisting of —NR$^5$CO—, —NR$^5$COR$^5$, —CONR$^5$—, —N=N—, —NH—CO—NH—, —NH—CS—NH—, —CO—O—, CO—O—CH$_2$—, —SO$_2$NH—, —NH—SO$_2$—, —C≡C—, —O—CH$_2$—CO—, —OCH$_2$CH$_2$O—, —CH(OH)—, and —NO$_2$ bridging groups,
R$^2$ and R$^3$ are each independently selected from the group consisting of H, and —NR$^5$COR$^5$;
R$^4$ is selected from the group consisting of halogen, C$_{1-6}$ alkyl, O—C$_{1-6}$ alkyl, —CN, —NH$_2$, and —NO$_2$; and
R$^5$ independently represents hydrogen, heteroaryl, or aryl, wherein the heteroaryl or aryl group may be optionally substituted by one or more R$^4$ groups.

3. The compound of formula (IIa) according to claim 1, wherein

R is H;
R¹ is NR⁵COR⁵; is selected from the group consisting of —NR⁵CO—, —NR⁵COR⁵, —CONR⁵—, —N=N—, —NH—CO—NH—, —NH—CS—NH—, —CO—O—, CO—O—CH₂—, —SO₂NH—, —NH—SO₂—, —C≡C—, —O—CH₂—CO—, —OCH₂CH₂O—, —CH(OH)—, and —NO₂ bridging groups;
R² is —NR⁵COR⁵;
R³ is H;
R⁴ is selected from the group consisting of hydrogen, halogen, C₁₋₆ alkyl, O—C₁₋₆ alkyl, —CN, —NH₂, and —NO₂; and
R⁵ independently represents hydrogen or thiophene or phenyl, wherein the thiophene or phenyl group may be optionally substituted by one or more R⁴ groups.

4. The compound of formula (IIa) according to claim 1, wherein
R is H;
R₁ is NR⁵COR⁵; is selected from the group consisting of —NR⁵CO—, —NR⁵COR⁵, —CONR⁵—, —N=N—, —NH—CO—NH—, —NH—CS—NH—, —CO—O—, CO—O—CH₂—, —SO₂NH—, —NH—SO₂—, —C≡C—, —O—CH₂—CO—, —OCH₂CH₂O—, —CH(OH)—, and —NO₂ bridging groups;
R₂ is —NR⁵COR⁵;
R₃ is H;
R⁴ is selected from the group consisting of hydrogen, halogen, and —NO₂; and
R⁵ represents hydrogen or phenyl, wherein the phenyl group may be optionally substituted by one or more R⁴ groups.

5. The compound of formula (IIb) according to claim 1, wherein:
R is H; is H or alkyl;
X is NH₂; is NH₂ or —NR⁵COR⁵;
R¹ is NR⁵COR⁵; is selected from the group consisting of —NHR⁴, OR⁴, —NH—CR⁴=CR⁴—, —NR⁵—, —NR⁵CH₂—, —CH₂NR⁵—, —NR⁵CO—, —NR⁵COR⁵—, —CONR⁵—, —N=N—, —NH—CO—NH—, —NH—CS—NH—, —CO—O—, CO—O—CH₂—, —SO₂NH—, —NH—SO₂—, —C≡C—, —O—CH₂—CO—, —OCH₂CH₂O—, —CH(OH)—, and —NO₂ bridging groups;
R² and R³ are each independently selected from the group consisting of H and —NR⁵COR⁵;
R⁴ is selected from the group consisting of halogen, C₁₋₆ alkyl, O—C₁₋₆ alkyl, —CN, —NH₂, and —NO₂; and
R⁵ independently represents hydrogen, C₁₋₆ alkyl, heteroaryl, or aryl, wherein the heteroaryl or aryl group may be optionally substituted by one or more R⁴ groups.

6. The compound of formula (IIb) according to claim 1, wherein
R is H; is H or methyl;
X is NH₂; is NH₂ or —NR⁵COR⁵;
R² and R³ are H;
R¹ is NR⁵COR⁵; is selected from the group consisting of —NHR⁴, OR⁴, —NH—CR⁴=CR⁴—, —NR⁵—, —NR⁵CH₂—, —CH₂NR⁵—, —NR⁵CO—, —NR⁵COR⁵—, —CONR⁵—, —N=N—, —NH—CO—NH—, —NH—CS—NH—, —CO—O—, CO—O—CH₂—, —SO₂NH—, —NH—SO₂—, —C=C—, —O—CH₂—CO—, —OCH₂CH₂O—, —CH(OH)—, and —NO₂ bridging groups;
R⁴ is selected from the group consisting of halogen, C₁₋₆ alkyl, O—C₁₋₆ alkyl, —CN, —NH₂, and —NO₂; and
R⁵ independently represents hydrogen, methyl, thiophene, or phenyl, wherein the thiophene or phenyl group may be optionally substituted by one or more R⁴ groups.

7. The compound of formula (IIa) and (IIb) according to claim 1, wherein the compound is selected from the group consisting of:

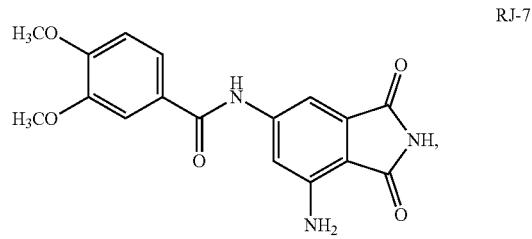

RJ-7

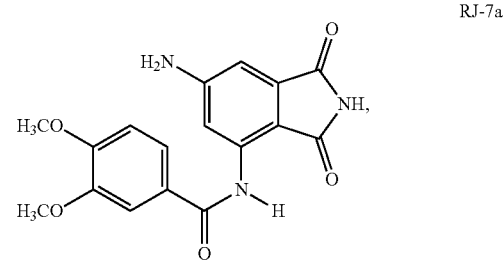

RJ-7a

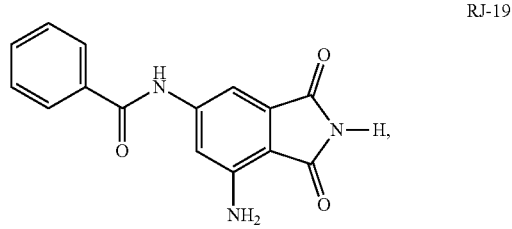

RJ-19

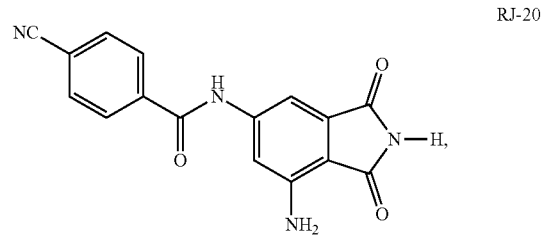

RJ-20

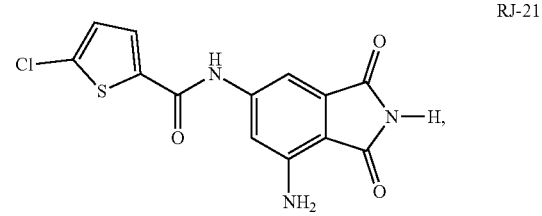

RJ-21

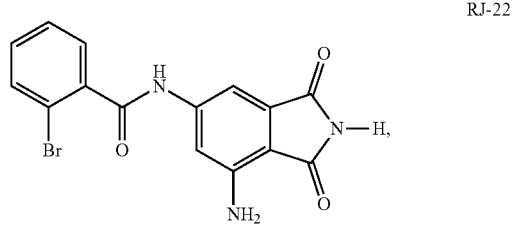

RJ-22

-continued
RJ-23
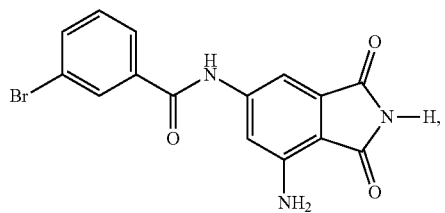
RJ-24
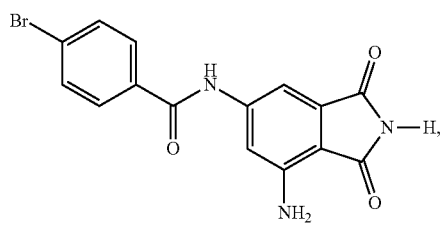
RJ-25
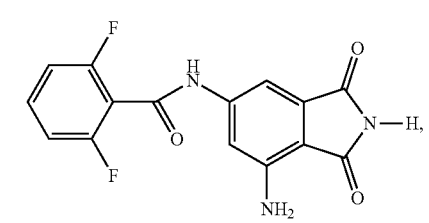
RJ-26
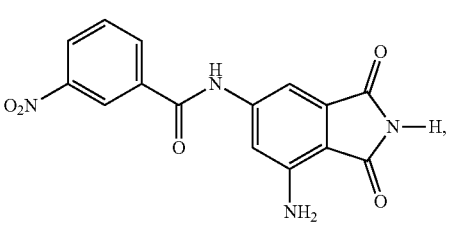
RJ-27
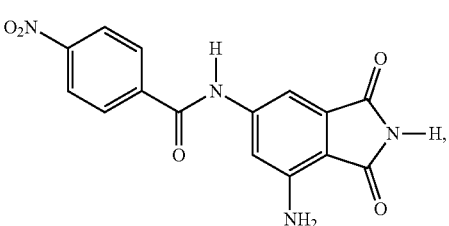
RJ-28
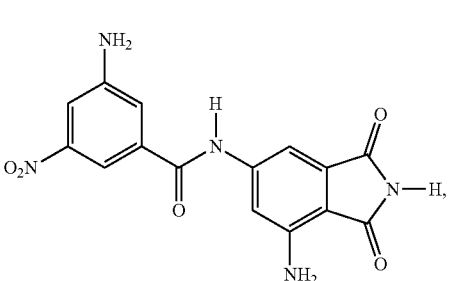
RJ-29
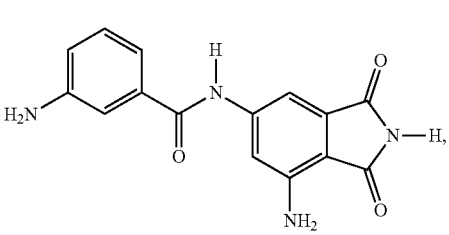
-continued
RJ-30
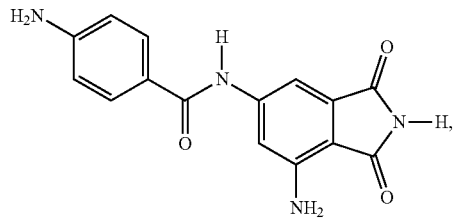
RJ-31
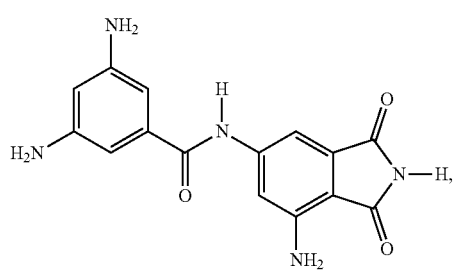
RJ-32
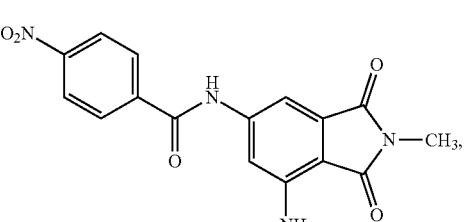
RJ-33
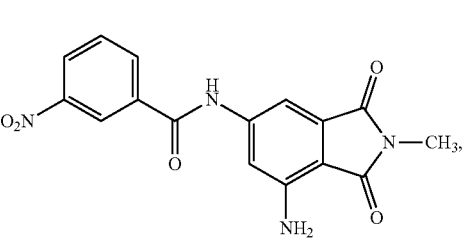
RJ-34
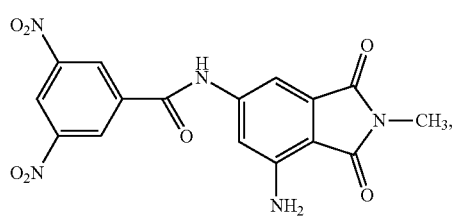
RJ-35
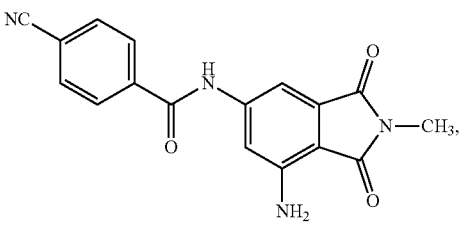
RJ-36
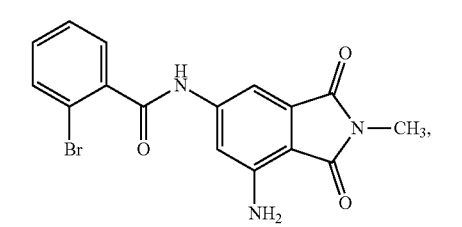

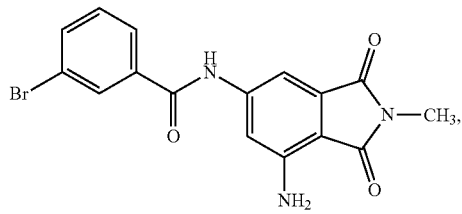
RJ-37
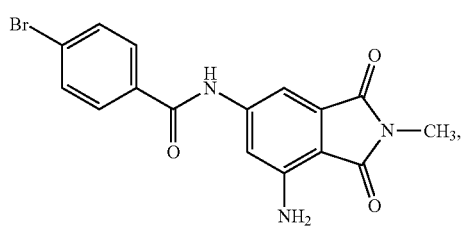
RJ-38
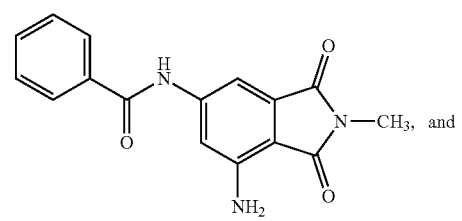
RJ-39
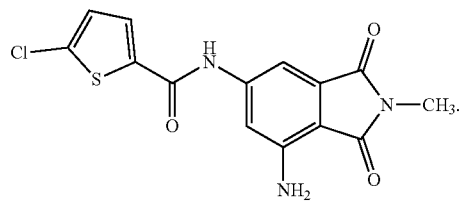
RJ-40
8. The compound of formula (IIb) according to claim 1, wherein the compound is selected from the group consisting of
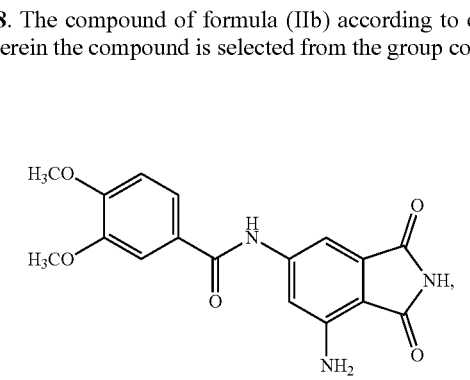
RJ-7
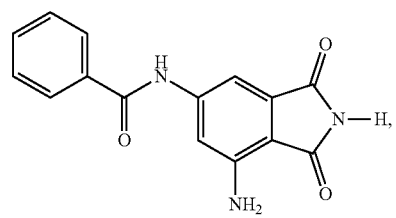
RJ-19
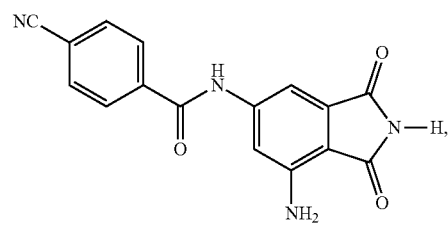
RJ-20
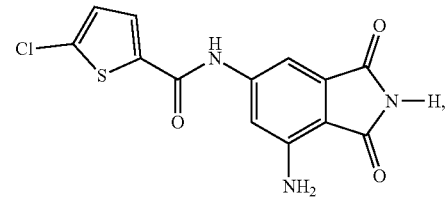
RJ-21
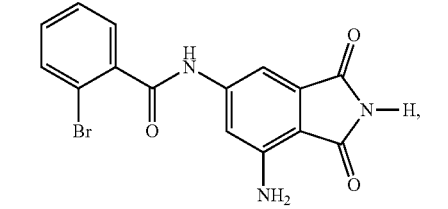
RJ-22
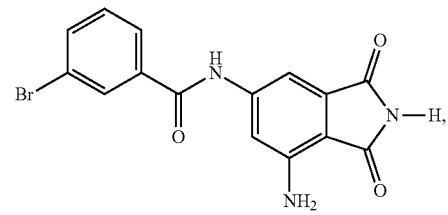
RJ-23
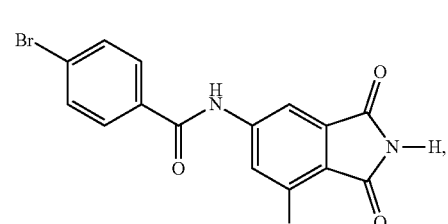
RJ-24
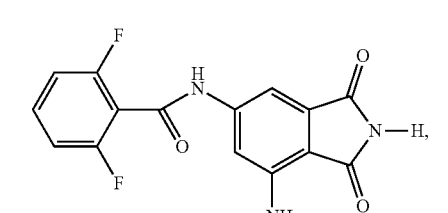
RJ-25
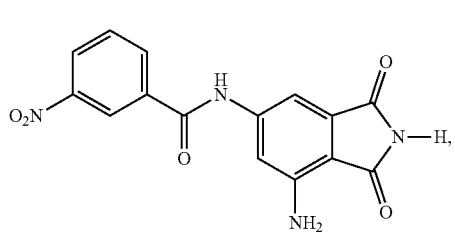
RJ-26

-continued

RJ-27
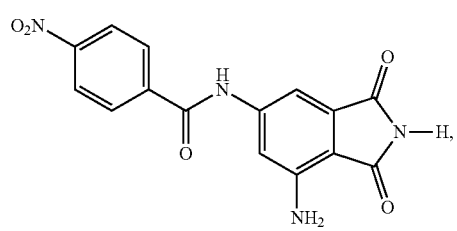

RJ-28
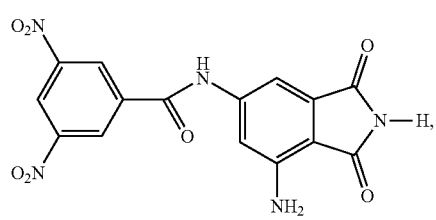

RJ-29
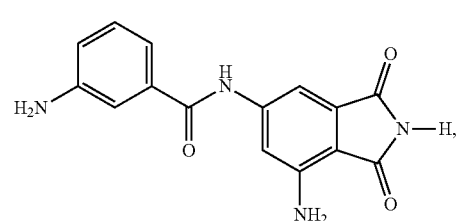

RJ-30
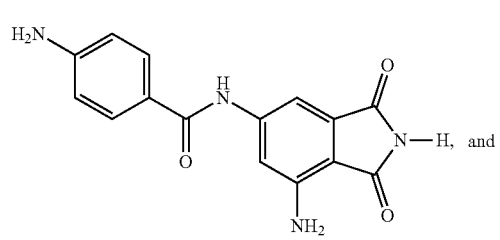

RJ-31
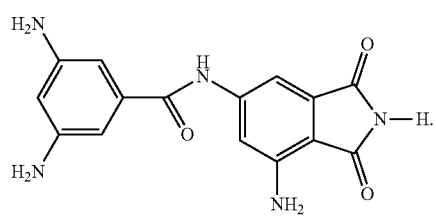

9. The compound of formula (IIa) according to claim 1, wherein the compound is

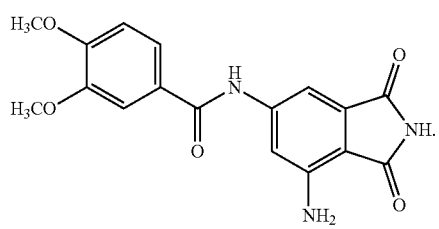 [SMILES: COc1ccc(C(=O)Nc2cc(N)c3c(c2)C(=O)NC3=O)cc1OC]

10. The compound of formula (IIa) according to claim 1, wherein the compound is

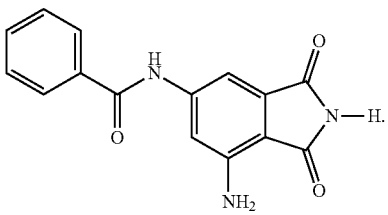

11. The compound of formula (IIa) according to claim 1, wherein the compound is

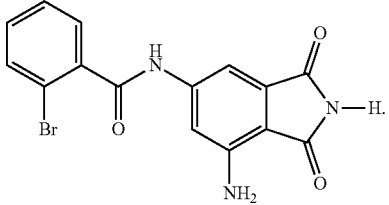

12. The compound of formula (IIa) according to claim 1, wherein the compound is:

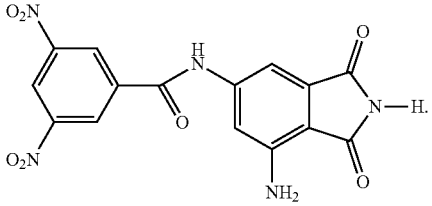

13. A pharmaceutical composition comprising the compound of claim 1, a stereoisomer, a pharmaceutically acceptable salt and/or a solvate thereof, and a pharmaceutically acceptable carrier.

14. The pharmaceutical composition of claim 13, wherein said pharmaceutical composition is suitable for enteral administration, oral administration, or parenteral administration.

* * * * *